(12) United States Patent
Kyle et al.

(10) Patent No.: US 11,319,599 B2
(45) Date of Patent: May 3, 2022

(54) GENETIC LOCI ASSOCIATED WITH REPRODUCTIVE GROWTH PHENOTYPES IN SOYBEAN AND METHODS OF USE

(71) Applicant: PIONEER HI-BRED INTERNATIONAL, INC., Johnston, IA (US)

(72) Inventors: Donald Earl Kyle, Princeton, IL (US); Landon Linn Ries, Armstrong, IA (US); Joshua Shendelman, Ankeny, IA (US); Hui Wang, Chatham (CA); John Bryan Woodward, Ankeny, IA (US); Ming Yang, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 41 days.

(21) Appl. No.: 15/773,678

(22) PCT Filed: Dec. 15, 2016

(86) PCT No.: PCT/US2016/066833
§ 371 (c)(1),
(2) Date: May 4, 2018

(87) PCT Pub. No.: WO2017/106447
PCT Pub. Date: Jun. 22, 2017

(65) Prior Publication Data
US 2018/0291471 A1 Oct. 11, 2018

Related U.S. Application Data
(60) Provisional application No. 62/269,775, filed on Dec. 18, 2015.

(51) Int. Cl.
| | | |
|---|---|---|
| *C12Q 1/6895* | (2018.01) | |
| *C12N 15/82* | (2006.01) | |
| *A01H 5/10* | (2018.01) | |
| *A01H 6/54* | (2018.01) | |
| *A01H 1/04* | (2006.01) | |
| *A01H 4/00* | (2006.01) | |

(52) U.S. Cl.
CPC ............ *C12Q 1/6895* (2013.01); *A01H 1/04* (2013.01); *A01H 4/005* (2013.01); *A01H 5/10* (2013.01); *A01H 6/542* (2018.05); *C12N 15/827* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS 9,951,391 B2 * 4/2018 Forth .................. C12Q 1/6895

FOREIGN PATENT DOCUMENTS

WO 2014/149920 A1 9/2014

OTHER PUBLICATIONS

Cheng, Lirui, et al.: "Genetic analysis and QTL detection of reproductive period and post-flowering photoperiod responses in soybean", Theoretical and Applied Genetics; International Journal of Plant Breeding Research, Springer, Berlin, DE, vol. 123, No. 3, May 10, 2011 (May 10, 2011), pp. 421-429.
Hyten, David L., et al.: "A High Density Integrated Genetic Linkage Map of Soybean and the Development of a 1536 Universal Soy Linkage Panel for Quantitative Trait Locus Mapping", Crop Science, vol. 50, No. 3, Jan. 1, 2010 (Jan. 1, 2010), p. 960.
Kong, F., et al.: "Two Coordinately Regulated Homologs of Flowering Locus T Are Involved in the Control of Photoperiodic Flowering in Soybean", Plant Physiology, vol. 154, No. 3, Nov. 1, 2010 (Nov. 1, 2010), pp. 1220-1231.
Naoki, Yamanaka, et al.: "Quantitative trait locus analysis of flowerings times in soybean using a RFLP linkage map", Breeding Science, Japanese Society of Breeding, Tokyo, JP, vol. 50, No. 2, Jun. 1, 2000 (Jun. 1, 2000), pp. 109-115.
Suli, Sun, et al.: "QTLs for resistance to Phomopsis seed decay are associated with days to maturity in soybean (*Glycine max*)", Theoretical and Applied Genetics; International Journal of Plant Breeding Research, Springer, Berlin, DE, vol. 126, No. 8, May 24, 2013 (May 24, 2013), pp. 2029-2038.
DATABASE_EMBL Accession No. GF095849 (Dec. 16, 2008).
International Search Report and Written Opinion, International Application No. PCT/US2016/066833 dated Jan. 3, 2017.

* cited by examiner

*Primary Examiner* — Katherine D Salmon

(57) ABSTRACT

Various methods and compositions are provided for identifying and/or selecting a soybean plant or soybean germplasm with one or more preferred or desired reproductive growth phenotypes. In certain embodiments, the method comprises detecting at least one allele of one or more marker locus within or linked to a QTL associated with days to initiation of flowering. In other embodiments, the method additionally comprises detecting at least one allele of one or more marker locus within or linked to a QTL associated with days to maturity. In further embodiments, the method comprises crossing a selected soybean plant with a recurrent soybean parent plant. Further provided herein are marker loci, marker alleles, primers, probes, and kits suitable for identifying and/or selecting soybean plants or soybean germplasms with one or more reproductive growth phenotypes.

26 Claims, 5 Drawing Sheets
Specification includes a Sequence Listing.

| Marker Locus | Marker type | Chrome. (Linkage group) | Map position (cM) |
|---|---|---|---|
| BARC-031339-07054 | SNP | 18 (G) | 60.203 |
| BARC-029289-06142 | SNP | 18 (G) | 60.526 |
| BARC-058401-15272 | SNP | 18 (G) | 60.526 |
| BARC-061457-17222 | SNP | 18 (G) | 60.526 |
| Satt505 | SSR | 18 (G) | 60.527 |
| BARC-055619-13499 | SNP | 18 (G) | 60.531 |
| BARC-059363-15766 | SNP | 18 (G) | 60.536 |
| BARC-032557-08997 | SNP | 18 (G) | 60.537 |
| BARC-062495-17850 | SNP | 18 (G) | 60.588 |
| Satt199 | SSR | 18 (G) | 60.599 |
| G214_14 | RFLP | 18 (G) | 60.718 |
| Sat_223 | SSR | 18 (G) | 60.819 |
| BARC-062435-17786 | SNP | 18 (G) | 60.915 |
| BARC-058327-15227 | SNP | 18 (G) | 60.922 |
| Sat_260 | SSR | 18 (G) | 60.969 |
| BARC-050149-09404 | SNP | 18 (G) | 60.999 |
| BARC-050151-09423 | SNP | 18 (G) | 60.999 |
| BARC-060125-16403 | SNP | 18 (G) | 61.074 |
| BARC-055933-13863 | SNP | 18 (G) | 61.108 |
| Satt400 | SSR | 18 (G) | 61.514 |
| B151_2 | RFLP | 18 (G) | 62.042 |
| i8_3 | RFLP | 18 (G) | 62.19 |
| A073_1 | RFLP | 18 (G) | 62.462 |
| A584_1 | RFLP | 18 (G) | 62.462 |
| Mng078_1 | RFLP | 18 (G) | 62.864 |
| Mng177_1 | RFLP | 18 (G) | 62.864 |
| Mng217_1 | RFLP | 18 (G) | 62.864 |
| p40_5_1 | RFLP | 18 (G) | 62.864 |
| Sle_001 | RFLP | 18 (G) | 62.864 |
| BARC-013627-01181 | SNP | 18 (G) | 63.215 |
| Satt012 | SSR | 18 (G) | 63.444 |
| BARC-024105-04728 | SNP | 18 (G) | 63.77 |
| BARC-056635-14538 | SNP | 18 (G) | 63.923 |
| BARC-030493-06880 | SNP | 18 (G) | 63.952 |
| BARC-013627-01180 | SNP | 18 (G) | 64.095 |
| A816_1 | RFLP | 18 (G) | 64.116 |

Figure 1A

| | | | |
|---|---|---|---|
| BARC-015633-02774 | SNP | 18(G) | 64.255 |
| BARC-015643-02792 | SNP | 18(G) | 64.255 |
| BARC-015645-02795 | SNP | 18(G) | 64.255 |
| BARC-053469-11867 | SNP | 18(G) | 64.255 |
| BARC-019255-03845 | SNP | 18(G) | 64.959 |
| Satt503 | SSR | 18(G) | 64.96 |
| Sat_164 | SSR | 18(G) | 65.776 |
| A890_1 | RFLP | 18(G) | 65.811 |
| Satt517 | SSR | 18(G) | 66.393 |
| BARC-027694-06635 | SNP | 18(G) | 67.91 |
| Sat_143 | SSR | 18(G) | 68.095 |
| BARC-040429-07735 | SNP | 18(G) | 69.133 |
| BARC-040163-07672 | SNP | 18(G) | 69.503 |
| BARC-050613-09770 | SNP | 18(G) | 69.503 |
| BARC-051229-11029 | SNP | 18(G) | 69.58 |
| BARC-012683-00361 | SNP | 18(G) | 70.397 |
| BARC-024489-04936 | SNP | 18(G) | 70.624 |
| BARC-055139-13077 | SNP | 18(G) | 71.459 |
| Satt288 | SSR | 18(G) | 71.577 |
| BARC-017185-02246 | SNP | 18(G) | 71.778 |
| BARC-061783-18883 | SNP | 18(G) | 72.018 |
| BARC-054359-12524 | SNP | 18(G) | 72.47 |
| BARC-019001-03049 | SNP | 18(G) | 72.842 |
| BARC-048761-10703 | SNP | 18(G) | 72.842 |
| BARC-016867-02359 | SNP | 18(G) | 73.336 |
| BARC-015471-01977 | SNP | 18(G) | 73.39 |
| BARC-021407-04097 | SNP | 18(G) | 73.39 |
| T005_2 | RFLP | 18(G) | 73.588 |
| BARC-018441-03188 | SNP | 18(G) | 73.802 |
| BARC-054243-12386 | SNP | 18(G) | 74.24 |
| Satt612 | SSR | 18(G) | 74.678 |
| BARC-052045-11324 | SNP | 18(G) | 74.995 |
| BARC-042393-08251 | SNP | 18(G) | 75.325 |
| BARC-026013-05225 | SNP | 18(G) | 75.641 |
| A885_1 | RFLP | 18(G) | 75.777 |
| BARC-019001-03050 | SNP | 18(G) | 76.246 |
| K493_1 | RFLP | 18(G) | 76.479 |
| BARC-015063-02553 | SNP | 18(G) | 76.876 |
| BARC-017681-03105 | SNP | 18(G) | 77.373 |
| BARC-008223-00022 | SNP | 18(G) | 78.048 |
| BARC-018635-03211 | SNP | 18(G) | 78.11 |

Figure 1B

| | | | | |
|---|---|---|---|---|
| BARC-037195-06738 | SNP | 18(G) | 78.278 | |
| BARC-013509-00507 | SNP | 18(G) | 78.501 | |
| BARC-055851-13786 | SNP | 18(G) | 78.894 | |
| BARC-059017-15576 | SNP | 18(G) | 78.894 | |
| BARC-016503-02070 | SNP | 18(G) | 79.119 | |
| BARC-054089-12331 | SNP | 18(G) | 79.119 | |
| BARC-032277-08935 | SNP | 18(G) | 79.403 | |
| BARC-016935-02365 | SNP | 18(G) | 79.663 | |
| BARC-018537-02954 | SNP | 18(G) | 79.663 | |
| BARC-032365-08955 | SNP | 18(G) | 79.778 | |
| AF162283 | SSR | 18(G) | 79.793 | |
| BARC-032785-09037 | SNP | 18(G) | 80.96 | |
| BARC-041331-07965 | SNP | 18(G) | 80.96 | |
| BARC-041705-08069 | SNP | 18(G) | 80.96 | |
| bac1F11Rhnd | RFLP | 18(G) | 81.416 | |
| p28_13_2 | RFLP | 18(G) | 82.106 | |
| A245_2 | RFLP | 18(G) | 84.046 | |
| Sct_199 | SSR | 18(G) | 85.655 | |
| Satt472 | SSR | 18(G) | 85.983 | |
| BARC-048095-10484 | SNP | 18(G) | 86.585 | |
| BARC-038873-07372 | SNP | 18(G) | 87.301 | |
| A235_1 | RFLP | 18(G) | 87.646 | |
| L002_2 | RFLP | 18(G) | 88.398 | |
| Satt191 | SSR | 18(G) | 89.372 | |
| BARC-031343-07057 | SNP | 18(G) | 90.462 | |
| L154_1 | RFLP | 18(G) | 90.905 | |
| Sat_117 | SSR | 18(G) | 91.076 | |
| H3_54HE_1 | RFLP | 18(G) | 92.449 | |
| BARC-010491-00654 | SNP | 18(G) | 93.003 | |
| BARC-010495-00656 | SNP | 18(G) | 93.234 | |
| BARC-010497-00670 | SNP | 18(G) | 93.588 | |
| BARC-044741-08783 | SNP | 18(G) | 93.656 | |
| BARC-010255-00571 | SNP | 18(G) | 93.867 | |
| BARC-024251-04812 | SNP | 18(G) | 94.304 | |
| BARC-020069-04425 | SNP | 18(G) | 96.305 | ↑ |
| M2 | SNP | 18(G) | 96.41 | Maturity QTL |
| M1 | SNP | 18(G) | 96.76 | |
| BARC-062677-18004 | SNP | 18(G) | 97.315 | ↓ |
| A690_2 | RFLP | 18(G) | 98.443 | |
| Bng069_1 | RFLP | 18(G) | 99.391 | |
| BARC-062769-18043 | SNP | 18(G) | 100.159 | |

Figure 1C

| | | | |
|---|---|---|---|
| BARC-014799-01667 | SNP | 18(G) | 100.197 |
| Sct_187 | SSR | 18(G) | 100.374 |
| BARC-044363-08678 | SNP | 18(G) | 100.44 |
| BARC-031121-06998 | SNP | 18(G) | 100.921 |
| Sat_064 | SSR | 18(G) | 101.823 |
| BARC-030123-06813 | SNP | 18(G) | 101.849 |
| F4 | SNP | 18(G) | 102.18 |
| BARC-054735-12156 | SNP | 18(G) | 102.332 |
| F3 | SNP | 18(G) | 102.65 |
| BARC-050577-09750 | SNP | 18(G) | 102.729 |
| BARC-057845-14952 | SNP | 18(G) | 103.109 |
| BARC-031193-07008 | SNP | 18(G) | 103.116 |
| BARC-040605-07795 | SNP | 18(G) | 103.14 |
| BARC-013647-01216 | SNP | 18(G) | 103.219 |
| F1 | SNP | 18(G) | 103.23 |
| BARC-055537-13406 | SNP | 18(G) | 103.397 |
| BARC-050575-09746 | SNP | 18(G) | 103.403 |
| BARC-014379-01337 | SNP | 18(G) | 103.426 |
| BARC-039397-07314 | SNP | 18(G) | 103.553 |
| A378_1 | RFLP | 18(G) | 103.63 |
| Sat_372 | SSR | 18(G) | 104.012 |
| BARC-043995-08576 | SNP | 18(G) | 104.092 |
| L120_1 | RFLP | 18(G) | 104.192 |
| BARC-021603-04153 | SNP | 18(G) | 104.215 |
| L183_1 | RFLP | 18(G) | 104.419 |
| BARC-039091-07442 | SNP | 18(G) | 104.489 |
| BARC-039099-07444 | SNP | 18(G) | 104.53 |
| A586_2 | RFLP | 18(G) | 104.708 |
| BARC-064703-18782 | SNP | 18(G) | 105.531 |
| BARC-049989-09280 | SNP | 18(G) | 105.845 |
| BARC-065273-19301 | SNP | 18(G) | 106.163 |
| F2 | SNP | 18(G) | 106.41 |
| F7 | SNP | 18(G) | 106.82 |
| F8 | SNP | 18(G) | 106.85 |
| F5 | SNP | 18(G) | 106.86 |
| F6 | SNP | 18(G) | 107.09 |
| BARC-017669-03102 | SNP | 18(G) | 107.09 |
| BARC-013305-00475 | SNP | 18(G) | 107.09 |

Distal End (107.1 cM)

Flowering QTL

GENETIC LOCI ASSOCIATED WITH REPRODUCTIVE GROWTH PHENOTYPES IN SOYBEAN AND METHODS OF USE

FIELD

This disclosure relates to genetic loci associated with reproductive growth phenotypes in soybean plants and methods of identifying and/or selecting soybean plants or soybean germplasms that display one or more reproductive growth phenotypes.

BACKGROUND

Soybeans (*Glycine max* L. Merr.) are a major cash crop and investment commodity in North America and elsewhere. Soybean oil is one of the most widely used edible oils, and soybeans are used worldwide in both animal feed and in human food production. Additionally, soybean utilization is expanding to industrial, manufacturing, and pharmaceutical applications.

Soybean can grow across a wide range of latitudes due, in part, to the natural variation in the genes that control flowering time and maturity. Furthermore, the timings of soybean flowering and maturity are important agronomical traits that are associated with reproductive growth and yield. These traits are largely affected by the genetic response to environmental signals such as day-length and temperature. For example, soybean is a short-day plant, and while short days induce early flowering, long-day conditions delay flowering. Therefore, identification of novel genes that control flowering time and maturity and understanding their molecular basis is critical to improving soybean productivity and adaptation to various growing conditions. In turn, improving soybean adaptation for various growing regions and environmental conditions is crucial for maximizing yields.

Through selective breeding for flowering and maturity phenotypes, soybean varieties have been developed that are ideally suited for maximizing yield within a particular environment. Unfortunately, field testing for reproductive characteristics is laborious and challenging, and it cannot be accomplished until late in the plant life cycle. However, the use of molecular markers that are closely linked to loci that control flowering time as well as maturity allow for the selection of desired reproductive growth traits and expedite the introgression of desired alleles into elite cultivars.

Molecular markers have been used to selectively improve soybean crops through the use of marker assisted selection. Any detectible polymorphic trait can be used as a marker so long as it is inherited differentially and exhibits linkage disequilibrium with a phenotypic trait of interest. A number of soybean markers have been mapped and linkage groups created, as described in Cregan, P. B., et al., "An Integrated Genetic Linkage Map of the Soybean Genome" (1999) Crop Science 39:1464-90, and more recently in Choi, et al., "A Soybean Transcript Map: Gene Distribution, Haplotype and Single-Nucleotide Polymorphism Analysis" (2007) Genetics 176:685-96 and Hyten et al., "A High Density Integrated Linkage Map of Soybean and the Development of a 1536 Universal Soy Linkage Panel for Quantitative Trait Locus Mapping" (2010) Crop Sci. 50:960-968. Many soybean markers are publicly available at the USDA affiliated soybase website (http://www.soybase.org/).

Most plant traits of agronomic importance are polygenic, otherwise known as quantitative traits. A quantitative trait is controlled by several genes located at various locations, or loci, in the plant's genome. The multiple genes have a cumulative effect which contributes to the continuous range of phenotypes observed in many plant traits. These genes are referred to as quantitative trait loci (QTL). Recombination frequency measures the extent to which a molecular marker is linked with a QTL. Lower recombination frequencies, typically measured in centiMorgans (cM), indicate greater linkage between the QTL and the molecular marker. The extent to which two features are linked is often referred to as the genetic distance. The genetic distance is also typically related to the physical distance between the marker and the QTL; however, certain biological phenomenon (including recombinational "hot spots") can affect the relationship between physical distance and genetic distance. Generally, the usefulness of a molecular marker is determined by the genetic and physical distance between the marker and the selectable trait of interest.

In some cases, markers, such as such as Single Nucleotide Polymorphism (SNP) markers, can be found to exist in a certain region of a plant genome encompassing one or more QTL. In such cases, by determining the allele present at one of more of these marker loci, a plant can be identified and selected with certain desired traits. In some cases, multiple closely linked markers can be found to exist in certain regions of the plant genome encompassing one or more QTL. In such cases, by determining the allele present at each of those marker loci, a haplotype for that region of the plant genome can be determined. Further, by determining alleles or haplotypes present at multiple regions of the plant genome related to the same phenotypic trait, a marker profile for that trait can be determined. Such haplotype and marker profile information can be useful in identifying and selecting plants with certain desired traits.

Thus, there remains a need for means to identify genomic regions associated with reproductive stages in soybean plants. In particular, there remains a need to identify genomic regions associated with early flowering and/or maturity in soybean plants. The molecular markers and methods herein provide important tools for use in plant breeding programs to optimize or maximize the reproductive growth stage, and/or to develop varieties adapted for various growing regions or environments.

SUMMARY

Provided herein are marker loci suitable for the identification and/or selection of a soybean plant or soybean germplasm with a desired reproductive growth phenotype, such as early or late flowering and/or early or late maturity. For example, a method of selecting a soybean plant or soybean germplasm with one or more reproductive growth phenotypes is provided that includes (a) detecting in the soybean plant or soybean germplasm at least one allele of one or more marker locus within or linked to a quantitative trait locus (QTL) associated with days to initiation of flowering, wherein the allele is favorable for a first reproductive growth phenotype selected from the group consisting of early flowering and late flowering and (b) selecting the soybean plant or soybean germplasm comprising the at least one allele from step (a), thereby selecting a soybean plant with a first reproductive growth phenotype selected from the group consisting of early flowering and late flowering. In such methods, the one or more marker locus is selected from the group consisting of: (1) a marker locus localizing within a chromosomal interval flanked by and including marker locus Sct_187 and the distal end of chromosome 18; (2) a marker locus localizing within a genetic recombination distance of less than or equal to 5 cM from marker locus F2 on chromosome 18; (3) a marker locus localizing within a genetic recombination distance of less than or equal to 5 cM from marker locus F5 on chromosome 18; (4) a marker locus localizing within a genetic recombination distance of less than or equal to 5 cM from marker locus F6 on chromosome 18; (5) a marker locus localizing within a genetic recombination distance of less than or equal to 5 cM from marker locus F7 on chromosome 18; and (6) a marker locus localizing within a genetic recombination distance of less than or equal to 5 cM from marker locus F8 on chromosome 18. In some methods, the first reproductive growth type is early flowering.

Some methods provided herein further include the step of detecting in the soybean plant or soybean germplasm at least one allele of one or more marker locus within or linked to a QTL associated with days to maturity, wherein the allele is favorable for a second reproductive growth phenotype selected from the group consisting of early maturity, mid maturity and late maturity; and (b) the further step of selecting the soybean plant or soybean germplasm comprising the allele of one or more marker locus within or linked to the QTL associated with days to maturity, thereby selecting a soybean plant with a second reproductive growth phenotype selected from the group consisting of early maturity, mid maturity and late maturity. In such methods, the one or more marker locus is selected from the group consisting of: (1) a marker locus localizing within a chromosomal interval flanked by and including marker loci Satt472 and Sct_187 on chromosome 18; (2) a marker locus localizing within a genetic recombination distance of less than or equal to 5 cM from marker locus M1; (3) a marker locus localizing within a genetic recombination distance of less than or equal to 5 cM from marker locus M2; (4) marker locus M1; and (5) marker locus M2.

Also provided herein is a method of selecting a soybean plant or soybean germplasm with an extended reproductive growth stage that includes (a) isolating a first polynucleotide from the soybean plant or soybean germplasm, wherein the first polynucleotide comprises at least one allele of one or more marker locus within or linked to a QTL associated with days to initiation of flowering, wherein the allele is favorable for an early flowering reproductive growth phenotype, and (b) selecting the soybean plant or soybean germplasm comprising the at least one allele from step (a), thereby selecting a soybean plant with early flowering. In such methods, the one or more marker locus is selected from the group consisting of: (1) a marker locus localizing within a chromosomal interval flanked by and including marker locus Sct_187 and the distal end of chromosome 18; (2) a marker locus localizing within a genetic recombination distance of less than or equal to 5 cM from marker locus F2 on chromosome 18; (3) a marker locus localizing within a genetic recombination distance of less than or equal to 5 cM from marker locus F5 on chromosome 18; (4) a marker locus localizing within a genetic recombination distance of less than or equal to 5 cM from marker locus F6 on chromosome 18; (5) a marker locus localizing within a genetic recombination distance of less than or equal to 5 cM from marker locus F7 on chromosome 18; and (6) a marker locus localizing within a genetic recombination distance of less than or equal to 5 cM from marker locus F8 on chromosome 18.

Some methods further comprise the step of isolating a second polynucleotide from the soybean plant or soybean germplasm, wherein the second polynucleotide comprises at least one allele of one or more marker locus within or linked to a QTL associated with days to maturity, wherein the allele is favorable for a reproductive growth phenotype selected from the group consisting of early maturity, mid maturity and late maturity, and the step of selecting the soybean plant or soybean germplasm comprising the allele of one or more marker locus within or linked to the QTL associated with days to maturity, thereby selecting a soybean plant with a reproductive growth phenotype selected from the group consisting of early maturity, mid maturity and late maturity. In such methods, the one or more marker locus within or linked to the QTL associated with days to maturity phenotype is selected from the group consisting of: (1) a marker locus localizing within a chromosomal interval flanked by and including marker loci Satt472 and Sct_187 on chromosome 18; (2) a marker locus localizing within a genetic recombination distance of less than or equal to 5 cM from marker locus M1; (3) a marker locus localizing within a genetic recombination distance of less than or equal to 5 cM from marker locus M2; (4) marker locus M1; and (5) marker locus M2.

Also provided herein is a method of selecting a soybean plant or soybean germplasm with an extended reproductive growth stage, the method comprising:

(a) detecting in the soybean plant or soybean germplasm at least one favorable allele of one or more marker locus within or linked to a QTL associated with days to initiation of flowering, wherein the allele is favorable for an early flowering reproductive growth phenotype, and wherein the one or more marker locus is selected from the group consisting of: (1) a marker locus localizing within a chromosomal interval flanked by and including marker locus Sct_187 and the distal end of chromosome 18; (2) a marker locus localizing within a genetic recombination distance of less than or equal to 5 cM from marker locus F2 on chromosome 18; (4) a marker locus localizing within a genetic recombination distance of less than or equal to 5 cM from marker locus F5 on chromosome 18; (5) a marker locus localizing within a genetic recombination distance of less than or equal to 5 cM from marker locus F6 on chromosome 18; (6) a marker locus localizing within a genetic recombination distance of less than or equal to 5 cM from marker locus F7 on chromosome 18; and (7) a marker locus localizing within a genetic recombination distance of less than or equal to 5 cM from marker locus F8 on chromosome 18;

(b) detecting in the soybean plant or soybean germplasm at least one favorable allele of one or more marker locus within or linked to a QTL associated with days to maturity, wherein the allele is favorable for a reproductive growth phenotype selected from the group consisting of mid maturity and late maturity, and wherein the one or more marker locus is selected from the group consisting of: (1) a marker locus localizing within a chromosomal interval flanked by and including marker loci Satt472 and Sct_187 on chromosome 18; (2) a marker locus localizing within a genetic recombination distance of less than or equal to 5 cM from marker locus M1; (3) a marker locus localizing within a genetic recombination distance of less than or equal to 5 cM from marker locus M2; (4) marker locus M1; and (5) marker locus M2; and (c) selecting the soybean plant or soybean germplasm comprising the at least one allele from step (a) and the at least one allele from step (b), thereby selecting a soybean plant with early flowering and mid or late maturity.

A kit for selecting at least one soybean plant by marker assisted selection of a QTL associated with days to initiation of flowering is also provided that includes: (a) primers or probes for detecting a polymorphism in the soybean genome, wherein the physical position of the polymorphism is selected from the group consisting of 60/914,550 base pairs (bp) on chromosome 18, 61,796,264 bp on chromosome 18, 60,840,873 bp on chromosome 18, 60,745,556 bp on chromosome 18, 61,963,221 bp on chromosome 18, 62,111,333 bp on chromosome 18, 61,948,911 bp on chromosome 18, 61,948,986 bp on chromosome 18, and a combination thereof; and (b) instructions for using the primers or probes to detect the marker loci and correlating the marker loci with predicted number of days from planting to the initiation of flowering.

BRIEF DESCRIPTION OF THE DRAWINGS

FIG. 1A illustrates a genetic map comprising a portion of chromosome 18 of the soybean genome. Map positions are provided in centiMorgans (cM) using a genetic map based upon Hyten et al., "A High Density Integrated Linkage Map of Soybean and the Development of a 1536 Universal Soy Linkage Panel for Quantitative Trait Locus Mapping" (2010) Crop Sci. 50:960-968, and is also available at the USDA affiliated soybase website (http://www.soybase.org/).

FIG. 1B is a continuation of FIG. 1A and illustrates a genetic map comprising a portion of chromosome 18 of the soybean genome.

FIG. 1C is a continuation of FIG. 1B and illustrates a genetic map comprising a portion of chromosome 18 of the soybean genome comprising loci associated with days to maturity.

SUMMARY OF BIOLOGICAL SEQUENCES

Figure 1D:
FIG. 1D is a continuation of FIG. 1C and illustrates a genetic map comprising a portion of chromosome 18 of the soybean genome comprising loci associated with days to initiation of flowering or days to maturity.

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with the World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NOs: 1-4 comprise nucleotide sequences of regions of the soybean genome, each capable of being used as a probe or primer, either alone or in combination, for the detection of a marker locus F1 on chromosome 18 (LG-G). In certain methods, SEQ ID NOs: 1 and 2 are used as primers and SEQ ID NOs: 3 and 4 are used as allele specific probes.

SEQ ID NOs: 5-8 comprise nucleotide sequences of regions of the soybean genome, each capable of being used as a probe or primer, either alone or in combination, for the detection of a marker locus F2 on chromosome 18 (LG-G). In certain methods, SEQ ID NOs: 5 and 6 are used as primers and SEQ ID NOs: 7 and 8 are used as allele specific probes.

SEQ ID NOs: 9-12 comprise nucleotide sequences of regions of the soybean genome, each capable of being used as a probe or primer, either alone or in combination, for the detection of a marker locus F3 on chromosome 18 (LG-G). In certain methods, SEQ ID NOs: 9 and 10 are used as primers and SEQ ID NOs: 11 and 12 are used as allele specific probes.

SEQ ID NOs: 13-16 comprise nucleotide sequences of regions of the soybean genome, each capable of being used as a probe or primer, either alone or in combination, for the detection of a marker locus F4 on chromosome 18 (LG-G). In certain methods, SEQ ID NOs: 13 and 14 are used as primers and SEQ ID NOs: 15 and 16 are used as allele specific probes.

SEQ ID NOs: 17-20 comprise nucleotide sequences of regions of the soybean genome, each capable of being used as a probe or primer, either alone or in combination, for the detection of a marker locus F5 on chromosome 18 (LG-G). In certain methods, SEQ ID NOs: 17 and 18 are used as primers and SEQ ID NOs: 19 and 20 are used as allele specific probes.

SEQ ID NOs: 21-24 comprise nucleotide sequences of regions of the soybean genome, each capable of being used as a probe or primer, either alone or in combination, for the detection of a marker locus F6 on chromosome 18 (LG-G). In certain methods, SEQ ID NOs: 21 and 22 are used as primers and SEQ ID NOs: 23 and 24 are used as allele specific probes.

SEQ ID NOs: 25-28 comprise nucleotide sequences of regions of the soybean genome, each capable of being used as a probe or primer, either alone or in combination, for the detection of a marker locus F7 on chromosome 18 (LG-G). In certain methods, SEQ ID NOs: 25 and 26 are used as primers and SEQ ID NOs: 27 and 28 are used as allele specific probes.

SEQ ID NOs: 29-32 comprise nucleotide sequences of regions of the soybean genome, each capable of being used as a probe or primer, either alone or in combination, for the detection of a marker locus F7 on chromosome 18 (LG-G). In certain methods, SEQ ID NOs: 29 and 30 are used as primers and SEQ ID NOs: 31 and 32 are used as allele specific probes.

SEQ ID NOs: 33-36 comprise nucleotide sequences of regions of the soybean genome, each capable of being used as a probe or primer, either alone or in combination, for the detection of a marker locus M1 on chromosome 18 (LG-G). In certain methods, SEQ ID NOs: 33 and 34 are used as primers and SEQ ID NOs: 35 and 36 are used as allele specific probes.

SEQ ID NOs: 37-40 comprise nucleotide sequences of regions of the soybean genome, each capable of being used as a probe or primer, either alone or in combination, for the detection of a marker locus M2 on chromosome 18 (LG-G).

In certain methods, SEQ ID NOs: 37 and 38 are used as primers and SEQ ID NOs: 39 and 40 are used as allele specific probes.

SEQ ID NO: 41 is the genomic DNA region encompassing marker locus F1 on chromosome 18 (LG-G).

SEQ ID NO: 42 is the amplicon produced by amplifying genomic DNA using SEQ ID NO: 1 as a forward or reverse primer in conjunction with SEQ ID NO: 2 as the other primer in the pair. This amplicon encompasses marker locus F1 on chromosome 18 (LG-G).

SEQ ID NO: 43 is the genomic DNA region encompassing marker locus F2 on chromosome 18 (LG-G).

SEQ ID NO: 44 is the amplicon produced by amplifying genomic DNA using SEQ ID NO: 5 as a forward or reverse primer in conjunction with SEQ ID NO: 6 as the other primer in the pair. This amplicon encompasses marker locus F2 on chromosome 18 (LG-G).

SEQ ID NO: 45 is the genomic DNA region encompassing marker locus F3 on chromosome 18 (LG-G).

SEQ ID NO: 46 is the amplicon produced by amplifying genomic DNA using SEQ ID NO: 9 as a forward or reverse primer in conjunction with SEQ ID NO: 10 as the other primer in the pair. This amplicon encompasses marker locus F3 on chromosome 18 (LG-G).

SEQ ID NO: 47 is the genomic DNA region encompassing marker locus F4 on chromosome 18 (LG-G).

SEQ ID NO: 48 is the amplicon produced by amplifying genomic DNA using SEQ ID NO: 13 as a forward or reverse primer in conjunction with SEQ ID NO: 14 as the other primer in the pair. This amplicon encompasses marker locus F4 on chromosome 18 (LG-G).

SEQ ID NO: 49 is the genomic DNA region encompassing marker locus F5 on chromosome 18 (LG-G).

SEQ ID NO: 50 is the amplicon produced by amplifying genomic DNA using SEQ ID NO: 17 as a forward or reverse primer in conjunction with SEQ ID NO: 18 as the other primer in the pair. This amplicon encompasses marker locus F5 on chromosome 18 (LG-G).

SEQ ID NO: 51 is the genomic DNA region encompassing marker locus F6 on chromosome 18 (LG-G).

SEQ ID NO: 52 is the amplicon produced by amplifying genomic DNA using SEQ ID NO: 21 as a forward or reverse primer in conjunction with SEQ ID NO: 22 as the other primer in the pair. This amplicon encompasses marker locus F6 on chromosome 18 (LG-G).

SEQ ID NO: 53 is the genomic DNA region encompassing marker locus F7 on chromosome 18 (LG-G).

SEQ ID NO: 54 is the amplicon produced by amplifying genomic DNA using SEQ ID NO: 25 as a forward or reverse primer in conjunction with SEQ ID NO: 26 as the other primer in the pair. This amplicon encompasses marker locus F7 on chromosome 18 (LG-G).

SEQ ID NO: 55 is the genomic DNA region encompassing marker locus F8 on chromosome 18 (LG-G).

SEQ ID NO: 56 is the amplicon produced by amplifying genomic DNA using SEQ ID NO: 29 as a forward or reverse primer in conjunction with SEQ ID NO: 30 as the other primer in the pair. This amplicon encompasses marker locus F8 on chromosome 18 (LG-G).

SEQ ID NO: 57 is the genomic DNA region encompassing marker locus M1 on chromosome 18 (LG-G).

SEQ ID NO: 58 is the amplicon produced by amplifying genomic DNA using SEQ ID NO: 33 as a forward or reverse primer in conjunction with SEQ ID NO: 34 as the other primer in the pair. This amplicon encompasses marker locus M1 on chromosome 18 (LG-G).

SEQ ID NO: 59 is the genomic DNA region encompassing marker locus M2 on chromosome 18 (LG-G).

SEQ ID NO: 60 is the amplicon produced by amplifying genomic DNA using SEQ ID NO: 37 as a forward or reverse primer in conjunction with SEQ ID NO: 38 as the other primer in the pair. This amplicon encompasses marker locus M2 on chromosome 18 (LG-G).

DETAILED DESCRIPTION

A novel quantitative trait locus (QTL) containing genes and other genetic elements that control days to initiation of flowering in soybean has been mapped to chromosome 18 (LG-G). Despite its close proximity to another QTL associated with days to maturity, the use of molecular markers within or linked to the QTL associated with days to initiation of flowering can be used to select a soybean plant or soybean germplasm for use in plant breeding programs to produce progeny soybean with a desired or preferred flowering time, such as early or late flowering, without affecting days to maturity. Thus, in certain aspects of this disclosure, marker loci, marker alleles, and/or haplotypes within or linked to the QTL associated with days to initiation of flowering and methods of their use are provided and can be used to select a soybean plant or soybean germplasm with a desired reproductive growth phenotype, such as early or late flowering. In other aspects, marker loci, marker alleles, and/or haplotypes within or linked to a QTL associated with days to maturity and methods of their use are provided, and can be used in combination with marker loci, marker alleles, and/or haplotypes within or linked to a QTL associated with days to initiation of flowering to identify and/or select a soybean plant or soybean germplasm for use in plant breeding programs to produce progeny soybean with a reproductive growth phenotype that is optimized for various growing regions or environments.

Before describing the present compositions and methods in detail, it is to be understood that this disclosure is not limited to particular embodiments, which can, of course, vary. It is also to be understood that the terminology used herein is for the purpose of describing particular embodiments only, and is not intended to be limiting.

In this disclosure, a number of terms and abbreviations are used. Certain definitions used in this disclosure and claims are provided below. In order to provide a clear and consistent understanding of the disclosure and claims, including the scope to be given such terms, the following definitions apply unless specifically stated otherwise.

In addition, the disclosure of each reference set forth herein is hereby incorporated by reference in its entirety.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include embodiments encompassed by the terms "consisting essentially of" and "consisting of." Similarly, the term "consisting essentially of" is intended to include embodiments encompassed by the term "consisting of."

"Agronomics," "agronomic traits," and "agronomic performance" refer to the traits (and underlying genetic elements) of a given plant variety that contribute to yield over the course of a growing season. Individual agronomic traits include reproductive growth, emergence vigor, vegetative vigor, stress tolerance, disease resistance or tolerance, insect resistance or tolerance, herbicide resistance, branching, flowering, seed set, seed size, seed density, standability, threshability, initiation of flowering, maturity and the like.

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant. An allele is "favorable" for a certain phenotypic trait if that allele positively correlates with that phenotypic trait. An allele is "unfavorable" for a certain phenotypic trait if that allele negatively correlates with that phenotypic trait.

The term "amplifying" in the context of nucleic acid amplification is any process whereby an additional copy or copies of a selected nucleic acid (or a transcribed form thereof) are produced. An "amplicon" is an amplified nucleic acid, e.g., a nucleic acid that is produced by amplifying a template nucleic acid by any available amplification method.

The term "associated" or "association" when used in reference to a marker, marker allele, and/or polymorphism and a phenotypic trait refers to any statistically significant correlation between the presence of a given allele of a marker locus and the phenotypic trait, which may be qualitative or quantitative.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment flanked by and including specific marker loci.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

A "distal end" of a chromosome refers to the mapping position on a genetic map that is most distal from the 0 cM position and indicates the downstream terminus of the chromosome.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic association or linkage relationships among loci on one or more chromosomes (or linkage groups) within a given species, generally depicted in a diagrammatic or tabular form.

"Genotype" is a description of the allelic state at one or more loci in a cell or organism.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Introgression" means the entry or introduction of a gene, QTL, marker, maker allele, haplotype, marker profile, trait, or trait locus from the genome of one plant into the genome of another plant.

The terms "label" and "detectable label" refer to a molecule capable of detection. A detectable label can also include a combination of a reporter and a quencher, such as are employed in FRET probes or TAQMAN® probes. The term "reporter" refers to a substance or a portion thereof that is capable of exhibiting a detectable signal, which signal can be suppressed by a quencher. The detectable signal of the reporter is, e.g., fluorescence in the detectable range. The term "quencher" refers to a substance or portion thereof that is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between two genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seeds sharing a common genotype at the specified locus (or loci) are bulked providing a subline that is genetically homogenous at identified loci important for a trait of interest (e.g., days to initiation of flowering, days to maturity, tolerance, etc.).

"Linkage" refers to the tendency for alleles to segregate together more often than expected by chance if their transmission was independent. Typically, linkage refers to alleles on the same chromosome. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A 1/100 probability of recombination per generation is defined as a genetic map distance of 1.0 centiMorgan (1.0 cM).

The genetic elements or genes located on a single chromosome segment are physically linked. In some embodiments, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosomal segment are also "genetically linked", typically within a genetic recombination distance of less than or equal to 50 cM, e.g., about 49, 40, 30, 20, 19, 18, 17, 16, 15, 14, 13, 12, 11, 10, 9, 8, 7, 6, 5, 4, 3, 2, 1, 0.75, 0.5, 0.25 cM or less. That is, two genetic elements within a single chromosomal segment undergo recombination during meiosis with each other at a frequency of less than or equal to about 50%, e.g., about 49%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.75%, 0.5%, 0.25% or less. "Closely linked" markers display a cross over frequency with a given marker of about 10% or less, e.g., 9%, 8%, 7%, 6%, 5%, 4%, 3%, 2%, 1%, 0.75%, 0.5%, 0.25% or less (the given marker locus is within about 10 cM of a closely linked marker locus, e.g., 9, 8, 7, 6, 5, 4, 3, 2, 1, 0.75, 0.5, 0.25 cM or less of a closely linked marker locus). Put another way, closely linked marker loci co-segregate at least about 90 the time, e.g., 91%, 92%, 93%, 94%, 95%, 96%, 97%, 98%, 99%, 99.5%, 99.75%, or more of the time.

When referring to the relationship between two genetic elements, such as a genetic element contributing to early flowering and a proximal marker, "coupling" phase linkage indicates the state where the favorable allele at the days to flowering locus is physically associated on the same chromosome strand as the favorable allele of the respective lined marker locus. In the coupling phase, both favorable alleles are inherited together by progeny that inherit the chromosome strand. In "repulsion" phase linkage, the favorable allele at the locus of interest (e.g., a QTL for days to initiation of flowering) is physically linked with an unfavorable allele at the proximal marker locus, and the two favorable alleles are not inherited together (i.e., the two loci are "out of phase" with each other).

"Linkage disequilibrium" is a non-random association of two or more alleles wherein the two or more alleles occur together at a greater frequency than expected from their individual frequencies.

"Linkage group" refers to traits or marker loci that co-segregate. A linkage group generally corresponds to a chromosomal region containing genetic material that encodes the traits or marker loci.

"Locus" is a defined segment of DNA.

A "management zone" is any specific area within a field that responds to management practices in a similar way. There are various criteria and ways to create management zones, including but not limited to using soil data, climate information, geographic data, and/or crop information in conjunction with an algorithm to identify areas of a field that are most similar. The computer can take thousands of numbers and find areas that are alike, cluster them together, and generate a map. Different zones can be defined by using different data inputs, but weighting inputs differently, by assigning different criteria, or by identifying different management practices of interest. For example a management zone for irrigation is probably not identical to a management zone for weed management for the same field in the same year. Management zones may also use the same inputs and criteria and yet differ across years.

A "map location," a "map position," or a "relative map position" is an assigned location on a genetic map relative to linked genetic markers where a specified marker can be found within a given species. Map positions are generally provided in cM. Unless otherwise indicated, genetic positions provided are based on the *Glycine max* consensus map v 4.0 as provided by Hyten et al. (2010) Crop Sci 50:960-968, and is also available at the USDA affiliated soybase website (http://www.soybase.org/). A "physical position" or "physical location" is the position, typically in nucleotide bases, of a particular nucleotide, such as a SNP nucleotide, on the chromosome. Unless otherwise indicated, the physical position within the soybean genome provided is based on the *Glycine max* v1.1 genome sequence described in Schmutz et al. (2010) Nature 463:178-183, available from the Phytozome website (http://phytozome.jgi.doe.gov/pz/portal.html) or from the GenBank website (http://www.ncbi.nlm.nih.gov/). With regard to physical position on a chromosome, closely linked markers can be separated, e.g., by about 1 megabase (MB; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less.

"Mapping" is the process of defining the association and relationships of loci through the use of genetic markers, populations segregating for the markers, and/or standard genetic principles of recombination frequency.

"Marker", "molecular marker" or "marker locus" is a term used to denote a nucleic acid or amino acid sequence that is sufficiently unique to characterize a specific locus on the genome. Any detectible polymorphic trait can be used as a marker so long as it is inherited differentially and exhibits non-random association with a phenotypic trait of interest.

"Marker assisted selection" refers to the process of selecting a desired trait or traits in a plant or plants by detecting one or more nucleic acids from the plant, where the nucleic acid is associated with or linked to the desired trait, and then selecting the plant or germplasm possessing those one or more nucleic acids.

"Maturity Group" is an agreed-on industry division of groups of varieties, based on the zones in which they are adapted primarily according to day length and/or latitude. Soybean varieties are grouped into 13 maturity groups, depending on the climate and latitude for which they are adapted. Soybean maturities are divided into relative maturity groups (denoted as 000, 00, 0, I, II, III, IV, V, VI, VII, VIII, IX, X, or 000, 00, 0, 1, 2, 3, 4, 5, 6, 7, 8, 9, 10). These maturity groups are given numbers, with numbers 000, 00, 0 and 1 typically being adapted to Canada and the northern United States, groups VII, VIII and IX being grown in the southern regions of the United States, and Group X is tropical. Within a maturity group are sub-groups. A subgroup is a tenth of a relative maturity group (for example 1.3 would indicate a group 1 and subgroup 3). Within narrow comparisons, the difference of a tenth of a relative maturity group equates very roughly to a day difference in maturity at harvest.

A "mixed defined plant population" refers to a plant population containing many different families and lines of plants. Typically, the defined plant population exhibits a quantitative variability for a phenotype that is of interest. "Multiple plant families" refers to different families of related plants within a population.

A "recurrent" plant or "recurrent parent" plant refers to a plant typically having a genetic background with favorable agronomic traits that is crossed with a soybean plant comprising a desired trait or allele, which is sometimes referred to as a "donor" plant or "donor parent" plant. Backcrossing then enables the breeder to transfer the desired trait or allele from the donor plant into the favored genetic background of the recurrent plant.

"Haplotype" refers to a combination of particular alleles present within a particular plant's genome at two or more linked marker loci, for instance at two or more loci on a particular linkage group. For instance, in one embodiment, two specific marker loci on chromosome 18 (LG-G) are used to define a haplotype for a particular plant. In still further embodiments, 3, 4, 5, 6, 7, 8, 9, 10, 11, 12, 13, 14, 15, 16, 17, 18, 19, 20, or more linked marker loci are used to define a haplotype for a particular plant.

As used herein, a "marker profile" means a combination of particular alleles present within a particular plant's genome at two or more marker loci which are not linked, for instance two or more loci on two or more different linkage groups or two or more chromosomes. For instance, in one embodiment, one marker locus on chromosome 18 (LG-G) and a marker locus on another linkage group are used to define a marker profile for a particular plant. In certain other embodiments a plant's marker profile comprises one or more haplotypes. In some embodiments, the marker profile encompasses two or more loci for the same trait, such as time to initiation of flowering. In other embodiments, the marker profile encompasses two or more loci associated with two or more traits of interest, such as days to initiation of flowering and a second trait of interest.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells, and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid sequence," "nucleic acid fragment," and "oligonucleotide" are used interchangeably herein to indicate a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide which is capable of acting as a point of initiation of nucleic acid synthesis or replication along a complementary strand when placed under conditions in which synthesis of a complementary strand is catalyzed by a polymerase.

Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Reproductive growth stage" or "reproductive stage" is a description of the characteristics associated with various phases of reproductive growth.

"R1" is the first reproductive growth stage when soybean begins to bloom by producing the first flower.

"Days to flowering QTL" or "QTL associated with days to initiation of flowering" refers to the genetic elements controlling the days to initiation of flowering (R1). The genetic elements controlling days to initiation of flowering include the soybean Flowering Locus T homologs, ft1a and ft1b. The QTL associated with days to initiation of flowering is mapped to chromosome 18 between about 106.4 cM and about 107.1 cM based on the Consensus 4.0 genetic map.

"R7" is the seventh reproductive growth stage when a soybean begins maturity. A soybean plant is identified as beginning maturity when it has one mature pod.

"R8" is the eighth and final reproductive growth stage when a soybean is fully mature. A soybean plant is identified as fully mature when 95% of the pods are mature.

"Days to maturity QTL" or "QTL associated with days to maturity" refers to the genetic elements controlling the time in which soybean plants enter into the R8 reproductive growth stage. The QTL associated with days to maturity is mapped to chromosome 18 at approximately 96 cM based on the Consensus 4.0 genetic map.

"Self-crossing" or "self-pollination" or "selfing" is a process through which a breeder crosses a plant with itself; for example, a second-generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

The term "yield" refers to the productivity per unit area of a particular plant product of commercial value. For example, yield of soybean is commonly measured in bushels of seed per acre or metric tons of seed per hectare per season. Yield is affected by both genetic and environmental factors.

An "isolated" or "purified" polynucleotide or polypeptide, or biologically active portion thereof, is substantially or essentially free from components that normally accompany or interact with the polynucleotide or polypeptide as found in its naturally occurring environment. Typically, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein, culture media, or other chemical components. Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Sambrook").

QTLs Associated with Reproductive Growth Traits in Soybean

Multiple QTLs have been identified as containing genes and other genetic elements that control the reproductive growth period of soybean. Further, molecular markers genetically linked to these QTL can be used to predict the reproductive growth phenotypes observed in these populations, such as days to initiation of flowering and days to maturity. In other words, these molecular markers can be used to identify and/or select soybean plants or soybean germplasms for breeding programs to produce soybean plants with an extended or maximized reproductive growth stage and/or to develop soybean varieties adapted for various growing regions or environments.

In one aspect of this disclosure, a novel QTL associated with days to initiation of flowering is provided. The number of days from planting to initiation of flowering (R1) marks the beginning of the reproductive growth phase of soybean. Thus, extending the reproductive period through manipulation of this QTL, and the marker loci encompassed by or linked to this QTL, is useful for maximizing yield potential of the soybean plant. However, it is important to evaluate soybean varieties in the correct environments. Utilizing markers associated with soybean reproductive growth that distinguish between early and late alleles for initiation of flowering provides the ability to segregate soybean populations into the correct testing environment, without having to conduct a preliminary progeny test on the line to identify an appropriate environment. It is also desirable to increase genetic diversity by crossing soybeans line with disparate reproductive habits, such as late flowering by early flowering crosses. This process has been utilized with limited success in the past due to the low frequency of desirable segregates that have a specific reproductive periods for the target area of adaptation environment. By utilizing molecular markers associated with early flowering, a breeder can identify plants in early generations which likely will have reproductive characteristics for the target environment, rather than having to phenotype and select a preferred reproductive growth phenotype in a previous growing season, therefore saving time and other resources.

In addition to flowering time, the number of days to maturity in soybean plays a significant role in determining final seed yield, and it is common for seed yield and the length of reproductive growth to have a positive correlation Like flowering time, extending the reproductive period through manipulation of QTLs, and the marker loci encompassed by or linked to these QTLs, can also maximize yield potential. As with early flowering, breeders can utilize molecular markers associated with soybean reproductive growth that distinguish between early and late alleles for days to maturity and have the ability to select soybean populations predicted to have the desired phenotypes without having to conduct a preliminary progeny test on the line.

It is therefore an object of this disclosure to provide molecular markers and methods for their use for identifying and/or selecting a soybean plant or soybean germplasm that displays one or more reproductive growth phenotypes. In certain aspects, the soybean plant or soybean germplasm is identified and/or selected based on the presence of marker alleles associated with a reproductive growth phenotype, such as early flowering or late flowering. A soybean plant with an early flowering phenotype will typically exhibit a decrease in the number of days from planting to the initiation of flowering as compared to a parental plant or other soybean plant with the marker allele associated with late flowering. In other aspects, marker loci localized within or genetically linked to a QTL associated with days to flowering are suitable for use with the present methods.

In a particular embodiment, the method comprises detecting in the soybean plant or soybean germplasm at least one allele of one or more marker locus within or linked to a QTL associated with days to initiation of flowering. In certain embodiments, it may be desirable to identify and/or select a soybean plant or soybean germplasm with an early flowering reproductive growth phenotype, and, therefore, the detected allele is favorable for early flowering. For example, selecting for an early flowering phenotype and extending the reproductive growth phase in soybeans grown in regions with longer growing seasons may result in increased seed yield. In other embodiments, it may be desirable to identify and/or select a soybean plant or soybean germplasm more suitable for regions with shorter growing seasons. In such embodiments, shortening the length of the reproductive growth phase in a soybean plant may be optimal. Thus, provided herein are methods suitable for identifying and/or selecting a soybean plant or soybean germplasm with a late flowering reproductive growth phenotype. Also provided are isolated polynucleotides and kits for use in identifying and/or detecting a soybean plant or soybean germplasm that displays early flowering. Also provided are soybean plants and soybean germplasms comprising at least one marker locus conferring early flowering or late flowering.

In other embodiments, the method comprises detecting in the soybean plant or soybean germplasm at least one allele of one or more marker locus within or linked to a QTL associated with days to maturity. In a particular embodiment, at least one marker allele associated with days to maturity is detected in addition to at least one marker allele associated with days to flowering. In such embodiments, the method includes the detection of at least one allele of one or more marker locus within or linked to the QTL associated with days to maturity. In some embodiments, the detected allele is favorable for a preferred or desired reproductive growth phenotype, such as early maturity, mid maturity or late maturity. For example, it may be desirable to select for a later maturity phenotype and extend the length of the reproductive growth phase in soybean plants to take advantage of geographic regions with longer growing seasons. Thus, if the preferred or desired reproductive growth phenotype is late maturity, then the favorable allele is one that positively correlates with the late maturity trait. A soybean plant comprising a marker allele favorable for an early maturity phenotype will exhibit a decreased number of days from planting to maturity as compared to a parental plant or other soybean plant comprising the marker allele associated with mid or late maturity.

Also provided are soybean plants and soybean germplasms comprising at least one marker allele, marker locus, haplotype, marker profile or QTL conferring early flowering or late flowering and/or at least one marker allele, marker locus, haplotype, marker profile or QTL conferring early maturity, mid maturity or late maturity.

In certain embodiments, soybean plants or soybean germplasm are identified that have at least one favorable allele, marker locus, haplotype or marker profile that positively correlates with a preferred or desired reproductive growth phenotype. However, in other embodiments, it is useful for exclusionary purposes during breeding to identify alleles, marker loci, haplotypes, or marker profiles that negatively correlate with a preferred or desired reproductive growth phenotype, for example, to eliminate such plants or germplasm from subsequent rounds of breeding. Thus, it is an object of this disclosure to provide molecular markers and methods allowing the selection of agronomic traits associated with time to initiation of flowering and/or days to maturity.

It is another object of this disclosure to provide methods for selecting a soybean plant or soybean germplasm in which is detected at least one favorable allele of one or more marker locus within or linked to a QTL associated with days to initiation of flowering and/or one or more marker locus within or linked to a QTL associated with days to maturity and then crossing the selected soybean plant or soybean germplasm to a recurrent soybean parent to produce a population of soybean progeny germplasm. In some embodiments, the QTL associated with days to initiation of flowering and/or the QTL associated with days to maturity will be introgressed into a subpopulation of the soybean progeny germplasm. In such embodiments, a progeny soybean plant grown from the subpopulation of progeny soybean germplasm will display an altered reproductive growth phenotype compared to the recurrent soybean parent or another soybean plant grown in the same field environment.

In addition to the marker loci described herein, any marker associated with a QTL associated with flowering time and/or maturity may be useful. Further, any suitable type of marker can be used, including Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers known in the art or phenotypic traits may also be used as markers in the methods. Nucleotide polymorphisms, including SNPs as well as insertions/deletions (INDELs) have been identified that are closely linked to and in linkage disequilibrium (LD) with the reproductive growth loci in soybean. These polymorphisms allow for marker-assisted selection (MAS) of these loci, expediting the creation and precise selection soybean plants with a desired reproductive growth phenotype. This will allow for more precision in developing varieties tailored to a particular environment.

While not intending to limiting, marker loci suitable for use with the present methods are provided in FIGS. 1A-1D, which depict a portion of a genetic map for chromosome 18 (LG-G) of soybean and provide the marker locus identifier as well as the genetic map positions of the marker loci. The genetic map positions provided in FIGS. 1A-1D are based on the soybean Consensus 4.0 (Hyten et al. 2010) available at the USDA affiliated soybase website (http://www.soybase.org/). Additionally, marker loci F1, F2, F3, F4, F5, F6, F7, F8, M1, and M2 of the instant disclosure have been included on the genetic map in FIGS. 1A-1D to indicate their genetic map locations in relation to the marker loci of the soybean Consensus 4.0 genetic map. One skilled in the art will recognize that the genetic map positions of the marker loci may vary when additional versions of the genetic map are published. One skilled in the art will also appreciate that the genetic map positions of the marker loci in FIGS. 1A-1D are based on a consensus map, which may be the same or different as compared to genetic mapping data of a particular soybean variety. In either case, the skilled artisan can easily determine the genetic map positions of the marker loci provided herein on any genetic map using routine genetic mapping and sequencing techniques.

The following provides a more detailed description of the marker loci suitable for use in the present methods.

Molecular Markers Associated with Days to Initiation of Flowering

A novel QTL has been identified on chromosome 18 (LG-G) (FIG. 1D) and contains two homologs of the *Arabidopsis thaliana* Flowering Locus T, ft1a and ft1b. This QTL is shown herein to contain genes and other genetic elements associated with the control of days to initiation of flowering in a soybean plant. Methods of detecting genetic markers located within the days to flowering QTL of the present disclosure and/or genetic markers linked to this QTL, and even other genetic markers closely linked to these markers, enable the identification and/or selection of a soybean plants or a soybean germplasm with an associated flowering time phenotype without affecting the time to maturity. Thus, provided herein are marker loci within or linked to the QTL associated with days to initiation of flowering time and are suitable for use in selecting a soybean plant or soybean progeny that displays a desired or preferred days to initiation of flowering phenotype. Also provided herein are marker loci, haplotypes and marker profiles associated with early flowering or late flowering.

In some embodiments, a soybean plant or a soybean germplasm is selected that has at least one favorable allele, marker locus, haplotype or marker profile that positively correlates with one or more reproductive growth phenotypes. In certain embodiments, a soybean plant or soybean germplasm is selected that has at least one allele of one or more marker locus that is within or linked to a QTL associated with days to initiation of flowering (e.g., the days to flowering QTL described in FIG. 1D), wherein the allele is favorable for a reproductive phenotype, such as early flowering or late flowering. In some embodiments, a favorable allele, marker locus, haplotype or marker profile positively correlates with early flowering. In other embodiments, a favorable allele, marker locus, haplotype or marker profile positively correlates with late flowering. In some aspects, a method for selecting a soybean plant or soybean germplasm with an extended reproductive growth stage is provided. In such aspects, a soybean plant or soybean germplasm is selected that has at least one allele of one or more marker locus that is linked a QTL associated with days to initiation of flowering, wherein the allele is favorable for an early flowering reproductive growth phenotype.

In certain aspects of this disclosure, a method of selecting a soybean plant or soybean germplasm with one or more reproductive growth phenotypes is provided and comprises detecting in the soybean plant or soybean germplasm at least one allele of one or more marker locus within or linked to a QTL associated with days to initiation of flowering. In one embodiment, the one or more allele detected is of one or more marker locus localizing on chromosome 18 (LG-G), such as the marker loci provided in FIGS. 1A-1D and Table 1. In other embodiments, the one or more allele detected is of one or more marker locus localizing within a chromosomal interval flanked by and including marker locus Sct_187 and the distal end of chromosome 18. In another embodiment, the one or more marker locus is localized within a chromosomal interval flanked by and including marker loci Sct_187 and BARC-13305-00475 on chromosome 18. In a preferred embodiment, the one or more marker locus is localized within a chromosomal interval flanked by and including marker loci BARC-049989-09280 and BARC-013305-00475 on chromosome 18 or a chromosomal interval flanked by and including marker loci F2 and BARC-013305-00475 on chromosome 18. In a more preferred embodiment, the one or more marker locus is localized within a chromosomal interval flanked by and including marker loci F2 and F6 on chromosome 18.

TABLE 1

Non-limiting list of marker loci associated with days to initiation of flowering.
Initiation of Flowering

| Marker Locus | Map Position (cM) | Physical Position (bp) | Early Flowering | Late Flowering |
|---|---|---|---|---|
| F1 | 103.23 | 60,914,550 | A | C |
| F2 | 106.41 | 61,796,264 | T | A |
| F3 | 102.65 | 60,840,873 | T | G |
| F4 | 102.18 | 60,745,556 | T | C |
| F5 | 106.86 | 61,963,221 | A | C |
| F6 | 107.09 | 62,111,333 | A | G |
| F7 | 106.82 | 61,948,911 | G | C |
| F8 | 106.85 | 61,948,986 | G | A |

In yet other embodiments, the one or more marker locus within or linked to the QTL associated with days to initiation of flowering is localized within a chromosomal interval flanked by and including marker loci: (i) F1 and F6 on chromosome 18; (ii) F1 and F5 on chromosome 18; (iii) F3 and F5 on chromosome 18; (iv) F2 and F5 on chromosome 18; (v) F7 and F5 on chromosome 18; (vi) BARC-049989-09280 and BARC-017669-03102 on chromosome 18; or (vii) Sat_064 and BARC-013305-00475 on chromosome 18. In yet other embodiments, the one or more marker locus is selected from the group consisting of Sct_187, BARC-044363-08678, BARC-031121-06998, Sat_064, BARC-030123-06813, BARC-054735-12156, BARC-050577-09750, BARC-057845-14952, BARC-031193-07008, BARC-040605-07795, BARC-013647-01216, BARC-055537-13406, BARC-050575-09746, BARC-014379-01337, BARC-039397-07314, A378_1, Sat_372, BARC-043995-08576, L120_1, BARC-021603-04153, L183_1, BARC-039091-07442, BARC-039099-07444, A586_2, BARC-064703-18782, BARC-049989-09280, BARC-065273-19301, BARC-017669-03102, BARC-013305-00475, F1, F2, F3, F4, F5, F6, F7, F8, and any combination thereof. In a preferred embodiment, the one or more marker locus is selected from the group consisting of F1, F2, F3, F4, F5, F6, F7, F8, and any combination thereof.

Markers that map closer to the QTL associated with days to initiation of flowering are generally preferred over markers that map farther from such QTL. Marker loci are especially useful when they are closely linked to the QTL associated with days to initiation of flowering. Thus, in one embodiment, a marker locus displays an inter-locus cross-over frequency of about 10% or less, about 9% or less, about 8% or less, about 7% or less, about 6% or less, about 5% or less, about 4% or less, about 3% or less, about 2% or less, about 1% or less, about 0.75% or less, about 0.5% or less, or about 0.25% or less with the to the QTL to which it is linked. Thus, the marker locus is separated from the QTL associated with days to initiation of flowering to which it is linked by about 10 cM, 9 cM, 8 cM, 7 cM, 6 cM, 5 cM, 4 cM, 3 cM, 2 cM, 1 cM, 0.75 cM, 0.5 cM, or 0.25 cM or less. Thus, in some embodiments, markers closely linked to the QTL associated with days to initiation of flowering, and markers that are genetically linked to these markers, are useful for identifying a soybean plant or soybean germplasm that displays early flowering or late flowering.

In further embodiments, the one or more allele detected is of one or more marker locus localizing within one or more of the genomic DNA regions of SEQ ID NOs: 41, 43, 45, 47, 49, 51, 53, or 55. In some embodiments, the one or more allele detected is of one or more marker locus localizing within 1 cM, 1.5 cM, 2 cM, 2.5 cM, 3 cM, 3.5 cM, 4 cM, 5 cM, 10 cM, 15 cM, or 20 cM of marker loci F1, F2, F3, F4, F5, F6, F7, or F8. In one embodiment, the one or more allele detected is of one or more marker locus localizing within a genetic recombination distance of less than or equal to 20 cM from marker locus on chromosome 18, preferably within a genetic recombination distance of less than or equal to 20 cM from a marker locus described in FIGS. 1A-1D. In other embodiments, the one or more marker locus is localized within a genetic recombination distance of less than or equal to 20 cM from marker locus F1 on chromosome 18. In yet other embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus F1 on chromosome 18. In certain embodiments, the one or more marker locus is localized within a genetic recombination distance of less than or equal to 20 cM from marker locus F2 on chromosome 18. In other embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus F2 on chromosome 18. In certain embodiments, the one or more marker locus is localized within a genetic recombination distance of less than or equal to 20 cM from marker locus F3 on chromosome 18. In other embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus F3 on chromosome 18. In certain embodiments, the one or more marker locus is localized within a genetic recombination distance of less than or equal to 20 cM from marker locus F4 on chromosome 18. In other embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus F4 on chromosome 18. In some embodiments, the one or more marker locus is localized within a genetic recombination distance of less than or equal to 20 cM from marker locus F5 on chromosome 18. In other embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus F5 on chromosome 18. In certain embodiments, the one or more marker locus is localized within a genetic recombination distance of less than or equal to 20 cM from marker locus F6 on chromosome 18. In other embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus F6 on chromosome 18. In certain aspects of this disclosure, the one or more marker locus is localized within a genetic recombination distance of less than or equal to 20 cM from marker locus F7 on chromosome 18. In others, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus F7 on chromosome 18. In certain embodiments, the one or more marker locus is localized within a genetic recombination distance of less than or equal to 20 cM from marker locus F8 on chromosome 18. In other embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus F8 on chromosome 18. In yet other embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from a favorable allele of marker locus F1, F2, F3, F4, F5, F6, F7, F8 or a combination thereof.

In some embodiments, the method comprises detecting one or more polymorphisms of one or more marker locus selected from the group consisting of Sct_187, BARC-044363-08678, BARC-031121-06998, Sat_064, BARC-030123-06813, BARC-054735-12156, BARC-050577-09750, BARC-057845-14952, BARC-031193-07008, BARC-040605-07795, BARC-013647-01216, BARC-055537-13406, BARC-050575-09746, BARC-014379-01337, BARC-039397-07314, A378_1, Sat_372, BARC-043995-08576, L120_1, BARC-021603-04153, L183_1, BARC-039091-07442, BARC-039099-07444, A586_2, BARC-064703-18782, BARC-049989-09280, BARC-065273-19301, BARC-017669-03102, BARC-013305-00475, F1, F2, F3, F4, F5, F6, F7, F8, and any combination thereof. In a preferred embodiment, the method comprises detecting one or more polymorphisms of one or more marker locus selected from the group consisting of F1, F2, F3, F4, F5, F6, F7, F8, and any combination thereof.

In some embodiments, the method comprises detecting a haplotype or a marker profile comprising two or more polymorphisms of or linked to marker loci selected from the group consisting of Sct_187, BARC-044363-08678, BARC-031121-06998, Sat_064, BARC-030123-06813, BARC-054735-12156, BARC-050577-09750, BARC-057845-14952, BARC-031193-07008, BARC-040605-07795, BARC-013647-01216, BARC-055537-13406, BARC-050575-09746, BARC-014379-01337, BARC-039397-07314, A378_1, Sat_372, BARC-043995-08576, L120_1, BARC-021603-04153, L183_1, BARC-039091-07442, BARC-039099-07444, A586_2, BARC-064703-18782, BARC-049989-09280, BARC-065273-19301, BARC-017669-03102, BARC-013305-00475, F1, F2, F3, F4, F5, F6, F7, F8, and any combination thereof. In a preferred embodiment, the method comprises detecting a haplotype or a marker profile comprising two or more polymorphisms of or linked to marker loci selected from the group consisting of F1, F2, F3, F4, F5, F6, F7, F8, and any combination thereof.

In some aspects, the method comprises detecting one or more polymorphisms having a physical position on chromosome 18 of the soybean genome based on the *Glycine max* Williams 82 V1.1 genome sequence (Schmutz et al. 2010) (see Table 1). In such aspects, the physical position is on chromosome 18 of the soybean genome and selected from the group consisting of 60/745,556 bp, 60,840,873 bp, 60,914,550 bp, 61,796,264 bp, 61,963,221 bp, 62,111,333 bp, 61,948,911 bp, 61,948,986 bp and any combination thereof. One skilled in the art will recognize that the physical positions of the polymorphisms (i.e., SNPs) may vary when additional versions of the soybean genomic sequence are published. One skilled in the art will also appreciate that the approximate physical positions of the SNPs in Table 1 are based on a publically available genomic sequence, which may be the same or different as compared to genomic sequence for a particular soybean variety. In either case, the skilled artisan can easily determine the approximate physical positions of the SNPs provided herein on any genomic sequence using sequencing and sequence analysis techniques, such as sequence alignments, BLAST searching, and the like.

In other embodiments, a haplotype or marker profile within, linked to or associated with the QTL associated with days to initiation of flowering comprises two or more polymorphisms described in Table 1. In some embodiments, the haplotype or the marker profile may comprise alleles favorable for early flowering. In other embodiments, the haplotype or the marker profile may comprise alleles favorable for late flowering, Alternatively, the haplotype or the marker profile may comprise a combination of alleles favorable for early flowering and alleles favorable for late flowering.

Also provided herein are alleles favorable for a reproductive growth phenotype selected from the group consisting of early flowering or late flowering. In some embodiments, the at least one favorable allele of one or more marker locus is selected from the group consisting of an early flowering allele of a marker provided in Table 1 and any combination thereof. In other embodiments, the at least one favorable allele of one or more marker locus is selected from the group consisting of a late flowering allele of a marker provided in Table 1 and any combination thereof. In yet other embodiments, a favorable allele for early flowering and a favorable allele for late flowering are detected in a soybean plant or soybean germplasm (i.e., the soybean plant or soybean germplasm is heterozygous).

In some embodiments, alleles favorable for the reproductive growth phenotypes early flowering or late flowering are provided. In one embodiment, a preferred or desired days to initiation of flowering phenotype is early flowering, and the at least one allele favorable for an early flowering phenotype comprises allele A of marker locus F1, allele T of marker locus F2, allele T of marker locus F3, allele T of marker locus F4, allele A of marker locus F5, allele A of marker locus F6, allele G of marker locus F7, allele G of marker locus F8 or any combination thereof. In other embodiments, a preferred or desired days to initiation of flowering phenotype is late flowering and that at least one allele favorable for a late flowering phenotype comprises allele C of marker locus F1, allele A of marker locus F2, allele G of marker locus F3, allele C of marker locus F4, allele C of marker locus F5, allele G of marker locus F6, allele C of marker locus F7, allele A of marker locus F8 or any combination thereof. In yet other embodiments, it is desired to select a soybean plant or soybean germplasm containing at least one allele favorable for early flowering and at least one allele favorable for late flowering.

In some embodiments, the method comprises isolating a polynucleotide from a soybean plant or soybean germplasm. For example, a method of selecting a soybean plant or soybean germplasm with one or more reproductive growth phenotypes and/or an extended reproductive growth phenotype is provided that comprises isolating a polynucleotide from the soybean plant or soybean germplasm. In such a method, the isolated polynucleotide comprises at least one of the alleles, marker loci, haplotypes, and/or marker profiles within, linked to or associated with a QTL associated with days to initiation of flowering as discussed herein. The isolation of the polynucleotide can be done using any standard DNA isolation technique known in the art.

Molecular Markers Associated with Days to Maturity

In another aspect of this disclosure, methods for extending or optimizing the reproductive growth phase in a soybean plant or soybean germplasm is provided. For example, as noted above, it may be desirable to select a soybean plant for growth in environments having a long growing season. While initiation of flowering (R1) begins reproductive growth of the soybean plant, full maturity, which begins at reproductive growth stage R8, marks the end of the reproductive growth phase of the soybean plant. Therefore, it may be desirable to select a soybean plant or soybean germplasm with a late maturity phenotype. Such a plant would exhibit increased days from planting until full maturity (R8) and therefore have a longer reproductive growth phase. Furthermore, if a soybean plant or soybean germplasm with an early flowering phenotype and a late maturity phenotype is selected, then such soybean plant or soybean germplasm displays a maximum length of the reproductive growth phase. In geographic regions with a long growing season, such as the southern regions of the U.S., a soybean plant displaying an extended or maximum reproductive growth phase will typically have greater seed yield. In contrast, it may be desirable to select a soybean plant for growth in environments having a short growing season. Therefore, it may be desirable to select a soybean plant or soybean germplasm with an early maturity phenotype. Such a plant would exhibit decreased days from planting until full maturity (R8) and therefore have a shorter reproductive growth phase. Therefore, identifying markers useful for the selection of early flowering or late flowering traits in addition to identifying markers that can be used for the selection of early, mid, or late maturity traits enable the breeder to optimize reproductive growth in soybean progeny produced in plant breeding programs and/or develop soybean varieties adapted for any growing region or environment.

It is therefore an object of this disclosure to provide molecular markers and methods of their use for selecting a soybean plant or soybean germplasm that displays one or more reproductive growth phenotypes in addition to days to initiation of flowering. In certain aspects, a soybean plant or soybean germplasm is selected with a days to maturity phenotype in addition to a days to initiation of flowering phenotype.

In some embodiments, a soybean plant or a soybean germplasm is selected that has at least one favorable allele, marker locus, haplotype or marker profile that positively correlates with one or more reproductive growth phenotypes in addition to at least one favorable allele, marker locus, haplotype or marker profile that positively correlates with one or more days to initiation of flowering phenotype. In such embodiments, a soybean plant or soybean germplasm is selected that has at least one allele of one or more marker locus within or linked to a QTL associated with days to maturity, wherein the allele is favorable for a reproductive growth phenotype, such as early maturity, mid maturity or late maturity. In some embodiments, a favorable allele, marker locus, haplotype or marker profile positively correlates with early maturity. In other embodiments, a favorable allele, marker locus, haplotype or marker profile positively correlates with mid maturity. In other embodiments, a favorable allele, marker locus, haplotype or marker profile positively correlates with late maturity. In some aspects, a method for selecting a soybean plant or soybean germplasm with an extended reproductive growth stage is provided. In such aspects, a soybean plant or soybean germplasm is selected that has at least one allele of one or more marker locus within or linked to the QTL associated with days to initiation of flowering, wherein the allele is favorable for an early flowering reproductive growth phenotype, and wherein the soybean plant or soybean germplasm also has at least one allele of one or more marker locus within or linked to a QTL associated with days to maturity, wherein the allele is favorable for an early, mid or late maturity reproductive growth phenotype. For example, a soybean plant or soybean germplasm can be selected for an extended or maximized reproductive growth stage that contains alleles favorable for early flowering and late maturity.

In a particular aspect, a method for selecting a soybean plant or soybean germplasm with one or more reproductive growth phenotypes is provided and comprises detecting in a soybean plant or soybean germplasm an allele of a marker locus within or linked to a QTL associated with days to maturity. In other embodiments, a method of selecting a soybean plant or soybean germplasm with one or more reproductive growth phenotypes is provided and comprises detecting in the soybean plant or soybean germplasm at least one allele of one or more marker locus within or linked to a QTL associated with days to initiation of flowering and detecting in the soybean plant or soybean germplasm at least one allele of one or more marker locus within or linked to a QTL associated with days to maturity. In this aspect, this additional detecting step can be performed prior to, simultaneous with or after the detection step described above for the days to flowering QTL.

In one embodiment, the one or more allele detected is of one or more marker locus localizing within any QTL associated with days to maturity known in the art (see, e.g., Cober et al. (1996) Crop Sci 36:601-605; Cober et al. (1996) Crop Sci 36:606-610; Asumadu et al. (1998) Ann Bot 82:773-778; Cober et al. (2001) Crop Sci 41:721-727; Abe et al. (2003) Crop Sci 43:1300-1304; Tasma & Shoemaker (2003) Crop Sci 41:319-328; Cober & Voldeng (2001) Crop Sci 41:698-701; Cober & Voldeng (2001) Crop Sci 41:1823-1926; and, Cober et al. (2010) Crop Sci 50:524-527). In a particular embodiment, the one or more allele detected is of one or more marker locus localizing on chromosome 18 (LG-G), such as the marker loci provided in FIGS. 1A-1D and Table 2. In some embodiments, the one or more allele detected is of one or more marker locus localizing within a chromosomal interval flanked by and including marker loci Satt472 and Sct_187 on chromosome 18. In another embodiment, the one or more marker locus is localized within a chromosomal interval flanked by and including marker loci Satt191 and BARC-062769-18043 on chromosome 18. In a preferred embodiment, the one or more marker locus is localized within a chromosomal interval flanked by and including marker loci BARC-010491-00654 and BARC-062769-18043 on chromosome 18 or a chromosomal interval flanked by and including marker loci BARC-024251-04812 and A690_2 on chromosome 18. In a more preferred embodiment, the one or more marker locus is localized within a chromosomal interval flanked by and including marker loci BARC-020069-04425 and BARC-062677-18004 on chromosome 18. In yet other embodiments, the one or more marker locus is selected from the group consisting of Satt472, BARC-048095-10484, BARC-038873-07372, A235_1, L002_2, Satt191, BARC-031343-07057, L154_1, Sat_117, H3_54HE_1, BARC-010491-00654, BARC-010495-00656, BARC-010497-00670, BARC-044741-08783, BARC-010255-00571, BARC-024251-04812, BARC-020069-04425, BARC-062677-18004, A690_2, Bng069_1, BARC-062769-18043, BARC-014799-01667, Sct_187, M1, M2 and any combination thereof. In a preferred embodiment, the one or more marker locus is selected from the group consisting of M1, M2 and a combination of M1 and M2.

TABLE 2

Non-limiting list of marker loci associated with days to maturity.
Days to Maturity

| Marker Locus | Map Position (cM) | Physical Position (bp) | Early | Mid | Late |
|---|---|---|---|---|---|
| M1 | 96.76 | 59,884,959 | C | T | T |
| M2 | 96.41 | 59,816,931 | C | C | T |

Markers that map closer to the QTL associated with days to maturity are generally preferred over markers that map farther from such a QTL. Marker loci are especially useful when they are closely linked to the QTL associated with days to maturity. Thus, in one embodiment, marker loci display an inter-locus cross-over frequency of about 10% or less, about 9% or less, about 8% or less, about 7% or less, about 6% or less, about 5% or less, about 4% or less, about 3% or less, about 2% or less, about 1% or less, about 0.75% or less, about 0.5% or less, or about 0.25% or less with the QTL associated with days to maturity to which it is linked. Thus, the loci are separated from the QTL associated with days to maturity to which they are linked by about 10 cM, 9 cM, 8 cM, 7 cM, 6 cM, 5 cM, 4 cM, 3 cM, 2 cM, 1 cM, 0.75 cM, 0.5 cM, or 0.25 cM or less. Thus, in some embodiments, markers closely linked to the QTL associated with days to maturity, and markers that are genetically linked to these markers, are useful for identifying a soybean plant or soybean germplasm that displays early maturity, mid maturity or late maturity.

In further embodiments, the one or more allele detected is of one or more marker locus localizing within one or more of the genomic DNA regions of SEQ ID NOs: 57 or 59. In some embodiments, the one or more allele detected is of one or more marker locus localizing within 1 cM, 1.5 cM, 2 cM, 2.5 cM, 3 cM, 3.5 cM, 4 cM, 5 cM, 10 cM, 15 cM, or 20 cM of marker loci M1 and M2 are provided. In one embodiment, the one or more allele detected is of one or more marker locus localizing within a genetic recombination distance of less than or equal to 20 cM from marker locus on chromosome 18, preferably within a genetic recombination distance of less than or equal to 20 cM from marker locus from FIGS. 1A-1D. In other embodiments, the one or more marker locus is localized within a genetic recombination distance of less than or equal to 20 cM from marker locus M1 on chromosome 18. In certain embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus M1 on chromosome 18. In other embodiments, the one or more marker locus is localized within a genetic recombination distance of less than or equal to 20 cM from marker locus M2 on chromosome 18. In certain embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from marker locus M2 on chromosome 18. In yet other embodiments, the one or more marker locus is localized within a genetic recombination distance of less than or equal to 15 cM, e.g., about 14, 13, 12, 11, 10, 9, 8, 7, 6, 5, 4, 3.5, 3, 2.5, 2, 1.5, 1, 0.75, 0.5, or 0.25 cM or less, from a favorable allele of marker locus M1, M2 or a combination thereof.

In some embodiments, the method comprises detecting one or more polymorphisms of one or more marker locus selected from the group consisting of Satt472, BARC-048095-10484, BARC-038873-07372, A235_1, L002_2, Satt191, BARC-031343-07057, L154_1, Sat_117, H3_54HE_1, BARC-010491-00654, BARC-010495-00656, BARC-010497-00670, BARC-044741-08783, BARC-010255-00571, BARC-024251-04812, BARC-020069-04425, BARC-062677-18004, A690_2, Bng069_1, BARC-062769-18043, BARC-014799-01667, Sct_187, M1, M2 and any combination thereof. In a preferred embodiment, the method comprises detecting one or more polymorphisms of one or more marker locus selected from the group consisting of M1, M2 and a combination of M1 and M2.

In some embodiments, the method comprises detecting a haplotype or a marker profile comprising two or more polymorphisms of or linked to marker loci selected from the group consisting of Satt472, BARC-048095-10484, BARC-038873-07372, A235_1, L002_2, Satt191, BARC-031343-07057, L154_1, Sat_117, H3_54HE_1, BARC-010491-00654, BARC-010495-00656, BARC-010497-00670, BARC-044741-08783, BARC-010255-00571, BARC-024251-04812, BARC-020069-04425, BARC-062677-18004, A690_2, Bng069_1, BARC-062769-18043, BARC-014799-01667, Sct_187, M1, M2 and any combination thereof. In a preferred embodiment, the method comprises detecting a haplotype or a marker profile comprising two or more polymorphisms of or linked to marker loci selected from the group consisting of M1, M2 and a combination of M1 and M2.

In some aspects, the method comprises detecting one or more polymorphisms having a physical position on chromosome 18 of the soybean genome based on the *Glycine max* Williams 82 V1.1 genome sequence (Schmutz et al. 2010). In such aspects, the physical position is on chromosome 18 of the soybean genome and selected from the group consisting of 59,884,959 bp, 59,816,931 bp and a combination thereof. One skilled in the art will recognize that the physical positions of the polymorphisms (i.e., SNPs) may vary when additional versions of the soybean genomic sequence are published. One skilled in the art will also appreciate that the approximate physical positions of the SNPs in Table 2 are based on a publically available genomic sequence, which may be the same or different as compared to genomic sequence for a particular soybean variety. In either case, the skilled artisan can easily determine the approximate physical positions of the SNPs provided herein on any genomic sequence using sequencing and sequence analysis techniques, such as sequence alignments, BLAST searching, and the like.

In other embodiments, the haplotype or marker profile within, linked to or associated with the QTL associated with days to maturity comprises two or more polymorphisms described in Table 2. In some embodiments, the haplotype or the marker profile may comprise alleles favorable for early maturity. In other embodiments, the haplotype or the marker profile may comprise alleles favorable for late maturity. In yet other embodiments, the haplotype or the marker profile may comprise alleles favorable for mid maturity. In other aspects, the haplotype or the marker profile may comprise a combination of alleles favorable for early maturity, mid maturity and/or late maturity.

Also provided herein are alleles favorable to a reproductive growth phenotype selected from the group consisting of early maturity, mid maturity and late maturity. In some embodiments, the at least one favorable allele of one or more marker loci is selected from the group consisting of an early maturity allele of a marker provided in Table 2 and any combination thereof. In other embodiments, the at least one favorable allele of one or more marker loci is selected from the group consisting of a late maturity allele of a marker provided in Table 2 and any combination thereof. In yet other embodiments, the at least one favorable allele of one or more marker loci is selected from the group consisting of a mid maturity allele of a marker provided in Table 2 and any combination thereof. In some embodiments, a soybean plant or soybean germplasm may be heterozygous for marker alleles of a days to maturity phenotype.

In some embodiments, alleles favorable for the reproductive growth phenotypes early maturity, mid maturity and/or late maturity are provided. In one embodiment, a preferred or desired days to maturity phenotype is early maturity and alleles favorable for an early maturity phenotype comprise allele C of marker locus M1, allele C of marker locus M2, or both. In other embodiments, a preferred or desired days to maturity phenotype is mid maturity and alleles favorable for a mid maturity phenotype comprise allele T of marker locus M1, allele C of marker locus M2 or both. In yet other embodiments, a preferred or desired days to maturity phenotype is late maturity and alleles favorable for a late maturity phenotype comprise allele T of marker locus M1, allele T of marker locus M2 or both. In yet other embodiments, it is desired to select a soybean plant or soybean germplasm containing at least one allele favorable for early maturity and at least one allele favorable for late maturity.

In some embodiments, the method comprises isolating a polynucleotide from the soybean plant or soybean germplasm. For example, a method of selecting a soybean plant or soybean germplasm with one or more reproductive growth phenotypes and/or an extended reproductive growth phenotype is provided that comprises isolating a polynucleotide from the soybean plant or soybean germplasm. In such a method, the isolated polynucleotide comprises at least one of the alleles, marker loci, haplotypes, and/or marker profiles within, linked to or associated with the QTL associated with days to maturity as discussed herein. The isolation of the polynucleotide can be done using any standard DNA isolation technique known in the art.

The detection of the at least one allele of one or more marker locus within or linked to a QTL associated with days to maturity can be performed before, during, or simultaneous with the detection of the at least one allele of one or more marker locus within or linked to a QTL associated with days to initiation of flowering. Any combination of the chromosomal intervals, alleles, marker loci or haplotypes described herein for the detection of the least one allele of one or more marker locus linked to a QTL associated with days to maturity is suitable for use with any combination of the chromosomal intervals, alleles, marker loci or haplotypes described herein for the detection of the least one allele of one or more marker locus within or linked to a QTL associated with days to initiation of flowering. For example, the detection of at least one allele of one or more marker locus within or linked to a QTL associated with days to initiation of flowering and the detection at least one allele of one or more marker locus within or linked to a QTL associated with days to maturity may comprise one or more marker locus:

(i) localized within a chromosomal interval flanked by and including marker locus Sct_187 and the distal end of chromosome 18;

(ii) localized within a chromosomal interval flanked by and including marker loci Sct_187 and BARC-13305-00475 on chromosome 18;

(iii) localized within a chromosomal interval flanked by and including marker loci BARC-049989-09280 and BARC-13305-00475 on chromosome 18;

(iv) localized within a chromosomal interval flanked by and including marker loci BARC-065273-19301 and BARC-013305-00475 on chromosome 18;

(v) localized within a chromosomal interval flanked by and including marker loci F2 and BARC-013305-00475 on chromosome 18;

(vi) localized within a chromosomal interval flanked by and including marker loci F2 and F6 on chromosome 18;

(vii) localized within a chromosomal interval flanked by and including marker loci F1 and F6 on chromosome 18;

(viii) localized within a chromosomal interval flanked by and including marker loci F1 and F5 on chromosome 18;

(ixi) localized within a chromosomal interval flanked by and including marker loci F3 and F5 on chromosome 18;

(x) localized within a chromosomal interval flanked by and including marker loci F2 and F5 on chromosome 18;

(xi) localized within a chromosomal interval flanked by and including marker loci F7 and F5 on chromosome 18;

(xii) localized within a chromosomal interval flanked by and including marker loci BARC-049989-09280 and BARC-017669-03102 on chromosome 18;

(xiii) localized within a chromosomal interval flanked by and including marker loci Sat_064 and BARC-013305-00475 on chromosome 18;

(xiv) selected from the group consisting of Sct_187, BARC-044363-08678, BARC-031121-06998, Sat_064, BARC-030123-06813, BARC-054735-12156, BARC- 050577-09750, BARC-057845-14952, BARC-031193-07008, BARC-040605-07795, BARC-013647-01216, BARC-055537-13406, BARC-050575-09746, BARC-014379-01337, BARC-039397-07314, A378_1, Sat_372, BARC-043995-08576, L120_1, BARC-021603-04153, L183_1, BARC-039091-07442, BARC-039099-07444, A586_2, BARC-064703-18782, BARC-049989-09280, BARC-065273-19301, BARC-017669-03102, BARC-013305-00475, F1, F2, F3, F4, F5, F6, F7, F8, and any combination thereof;

(xv) localizes within one or more of the genomic DNA regions of SEQ ID NOs: 41, 43, 45, 47, 49, 51, 53, or 55;

(xvi) localizes within 1 cM, 1.5 cM, 2 cM, 2.5 cM, 3 cM, 3.5 cM, 4 cM, 5 cM, 10 cM, 15 cM, or 20 cM of marker loci F1, F2, F3, F4, F5, F6, F7, or F8 or any combination thereof on chromosome 18;

(xvii) localizes within 1 cM, 1.5 cM, 2 cM, 2.5 cM, 3 cM, 3.5 cM, 4 cM, 5 cM, 10 cM, 15 cM, or 20 cM of a favorable allele of marker loci F1, F2, F3, F4, F5, F6, F7, or F8 or any combination thereof on chromosome 18; or (xviii) or any combination of (i)-(xvii); and used in combination with one or more marker locus:

(i) localized within a chromosomal interval flanked by and including marker loci Satt472 and Sct_187 on chromosome 18;

(ii) localized within a chromosomal interval flanked by and including marker loci Satt191 and BARC-062769-18043 on chromosome 18;

(iii) localized within a chromosomal interval flanked by and including marker loci BARC-010491-00654 and BARC-062769-18043 on chromosome 18;

(iv) localized within a chromosomal interval flanked by and including marker loci BARC-024251-04812 and A690_2 on chromosome 18;

(v) localized within a chromosomal interval flanked by and including marker loci BARC-020069-04425 and BARC-062677-18004 on chromosome 18;

(vi) selected from the group consisting Satt472, BARC-048095-10484, BARC-038873-07372, A235_1, L002_2, Satt191, BARC-031343-07057, L154_1, Sat_117, H3_54HE_1, BARC-010491-00654, BARC-010495-00656, BARC-010497-00670, BARC-044741-08783, BARC-010255-00571, BARC-024251-04812, BARC-020069-04425, BARC-062677-18004, A690_2, Bng069_1, BARC-062769-18043, BARC-014799-01667, Sct_187, M1, M2 and any combination thereof;

(vii) localizes within one or more of the genomic DNA regions of SEQ ID NOs: 57 or 59;

(viii) localizes within 1 cM, 1.5 cM, 2 cM, 2.5 cM, 3 cM, 3.5 cM, 4 cM, 5 cM, 10 cM, 15 cM, or 20 cM of marker loci M1, M2 or any combination thereof on chromosome 18;

(xix) localizes within 1 cM, 1.5 cM, 2 cM, 2.5 cM, 3 cM, 3.5 cM, 4 cM, 5 cM, 10 cM, 15 cM, or 20 cM of a favorable allele of marker loci M1, M2 or any combination thereof on chromosome 18; or (x) or any combination of (i)-(xix).

In certain embodiments, multiple marker loci that collectively make up a haplotype and/or a marker profile are investigated, for instance 2, 3, 4, 5, 6, 7, 8, 9, 10, 11, 12, 13, 14, 15, 16, 17, 18, 19, 20, 21, 22, 23, 24, 25, 26, 27, 28, 29, 30, or more marker loci. For example, a haplotype for early flowering and late maturity may comprise (i) allele A of marker locus F1, allele T of marker locus F2, allele T of marker locus F3, allele T of marker locus F4, allele A of marker locus F5, allele A of marker locus F6, allele G of marker locus F7, allele G of marker locus F8 or any combination thereof and (ii) allele T of marker locus M1, allele T of marker locus M2 or both. In another embodiment, a haplotype for early flowering and mid maturity may comprise (i) allele A of marker locus F1, allele T of marker locus F2, allele T of marker locus F3, allele T of marker locus F4, allele A of marker locus F5, allele A of marker locus F6, allele G of marker locus F7, allele G of marker locus F8 or any combination thereof and (ii) allele T of marker locus M1 and allele C of marker locus M2.

In other embodiments, the method involves detecting a marker profile comprising two or more marker loci, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 marker loci, or more. In some embodiments, the method uses marker assisted selection to stack two or more loci in a soybean plant or soybean germplasm. In some embodiments, the method uses a marker profile to produce a soybean plant or soybean germplasm having a desired predicted days to initiation of flowering. For instance, the desired predicted days to initiation of flowering is for a specific adapted growing zone or area of adaptability, including but not limited to day length, latitude, environmental class, management zone, maturity group and/or maturity. Furthermore, the method may use marker assisted selection to track a desired days to maturity trait in combination with the desired days to initiation of flowering in order to select soybean plants or soybean germplasms adapted for specific growing environments. In some embodiments, the area of adaptability may include using soybean to produce a second crop during a growing season. Second crops are commonly planted in areas with longer growing seasons; however, the selected crop may need different reproductive characteristics to be adapted for the second growing cycle in the season than it would for the first growing cycle of the season. Any method of environmental classification can be used, including but not limited to those described in U.S. Pat. No. 8,032,389, and Loeffler et al. (2005) Crop Sci 45:1708-1716, each of which is herein incorporated by reference in its entirety. In certain embodiments, the marker profile comprises two or more markers selected from the group consisting of F1, F2, F3, F4, F5, F6, F7, F8 and any combination thereof and two or more markers selected from the group consisting of M1, M2, and both M1 and M2. In further embodiments, the marker profile comprises markers from the set of markers described in FIGS. 1A-1D.

Suitable Techniques for the Detection of Molecular Markers

In certain aspects described herein, the method of selected a soybean plant or soybean germplasm displaying one or more reproductive growth phenotypes includes a detecting step. While not intending to be limited to any particular embodiment, provided herein are exemplary detection methods suitable for use with the present methods. For example, detecting may comprise analysis of sequence databases of soybean varieties (e.g., databases generated by genotype-by-sequence methods) in combination with archived phenotype information are suitable for the identification of suitable markers contained within or linked to a QTL associated with days to initiation of flowering or a QTL associated with days to maturity.

In another embodiment, the method of detecting comprises DNA sequencing of at least one of the marker loci provided herein. As used herein, "sequencing" refers to sequencing methods for determining the order of nucleotides in a molecule of DNA. Any DNA sequencing method known in the art can be used in the methods provided herein. Non-limiting examples of DNA sequencing methods useful in the methods provided herein include Next Generation Sequencing (NGS) technologies, for example, as described in Egan, A. N, et al. (2012) *American Journal of Botany* 99(2):175-185; genotyping by sequencing (GBS) methods, for example, as described in Elshire, R. J., et al. (2011) *PLoS ONE* 6(5):e19379; Molecular Inversion Probe (MIP) genotyping, as described, for example, in Hardenbol, P., et al. (2003) *Nature Biotechnology* 21(6):673-678; or high throughput genotyping by whole-genome resequencing, as described, for example in Huang, X et al., (2009) *Genome Research* 19:1068-1076.

In other aspects, the detecting may comprise designing a primer or probe that is complementary or partially complementary to at least a portion of the genomic DNA encompassing the marker locus and capable of specifically hybridizing to the marker locus of interest under at least moderately stringent conditions. In such aspects, the primer or probe optionally comprises a detectable label. Detecting may comprise isolating nucleic acids, amplifying the genomic DNA encompassing the marker locus or a portion of the genomic DNA encompassing the marker locus and detecting the resulting amplified marker amplicon. In some embodiments, the amplifying comprises admixing an amplification primer or amplification primer pair and, optionally at least one nucleic acid probe, with a nucleic acid isolated from the soybean plant or soybean germplasm, wherein the primer or primer pair and optional probe is complementary or partially complementary to at least a portion of the genomic DNA encompassing the marker locus and is capable of initiating DNA polymerization by a DNA polymerase using the soybean nucleic acid as a template; and, extending the primer or primer pair in a DNA polymerization reaction comprising a DNA polymerase and a template nucleic acid to generate at least one amplicon, such as an amplicon represented by any of SEQ ID NOs: 42, 44, 46, 48, 50, 52, 54, 56, 58, and 60. In particular embodiments, the detection comprises real time PCR analysis. For instance, provided herein are detection methods comprising amplifying a nucleic acid sequence comprising the marker locus of each marker allele within or linked to the QTLs described herein (e.g., the QTLs associated with days to initiation of flowering and/or days to maturity). In a particular embodiment, the amplifying step comprises amplification of at least a portion of the soybean genome selected from the group consisting of SEQ ID NOs: 41, 43, 45, 47, 49, 51, 53 and 55 for the detection of marker loci within or linked to the QTL associated with days to initiation of flowering and/or the group consisting of SEQ ID NOs: 57 and 59 for the detection of marker loci within or linked to the QTL associated with days to maturity.

In some embodiments, molecular markers are detected using a suitable amplification-based detection method. Typical amplification methods include various polymerase based replication methods, including the polymerase chain reaction (PCR), ligase mediated methods, such as the ligase chain reaction (LCR), and RNA polymerase based amplification (e.g., by transcription) methods. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage & Caruthers (1981) Tetrahedron Letts 22:1859-1862, e.g., using a commercially available automated synthesizer, e.g., as described in Needham-VanDevanter et al. (1984) Nucl Acids Res 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair, or probe. For example, primers can be designed using any suitable software program, such as LASERGENE® or Primer3.

The primers are not limited to generating an amplicon of any particular size. For example, the primers used to amplify the marker loci and alleles herein are not limited to amplifying the entire region of the relevant locus. In some embodiments, marker amplification produces an amplicon at least 20 nucleotides in length, or alternatively, at least 50 nucleotides in length, or alternatively, at least 100 nucleotides in length, or alternatively, at least 200 nucleotides in length, or alternatively, at least 300 nucleotides in length, or alternatively, at least 400 nucleotides in length, or alternatively, at least 500 nucleotides in length, or alternatively, at least 1000 nucleotides in length, or alternatively, at least 2000 nucleotides in length or more.

PCR, RT-PCR, and LCR are common amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous references, such as Mullis et al. (1987) U.S. Pat. No. 4,683,202; Arnheim & Levinson (1990) C&EN 36-47; Kwoh et al. (1989) Proc Natl Acad Sci USA 86:1173; Guatelli et al. (1990) Proc Natl Acad Sci USA 87:1874; Lomeli et al. (1989) J Clin Chem 35:1826; Landegren et al. (1988) Science 241:1077-1080; Van Brunt (1990) Biotechnology 8:291-294; Wu & Wallace (1989) Gene 4:560; Barringer et al. (1990) Gene 89:117; and Sooknanan & Malek (1995) Biotechnology 13:563-564.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype alleles, such as SNP alleles, are provided. Real-time amplification assays, including MB or TAQMAN® based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain embodiments, each allele-specific probe for a certain SNP locus is 13-18 nucleotides in length, duallabeled with a florescence quencher at the 3' end and either the 6-FAM (6-carboxyfluorescein) or VIC (4,7,2'-trichloro-7'-phenyl-6-carboxyfluorescein) fluorophore at the 5' end.

A non-limiting list of exemplary primers and probes suitable for use with the present methods is provided in Table 3. In certain embodiments, the detection step in the methods disclosed herein comprises PCR detection using amplification primers for amplifying at least a portion of one or more genomic regions of the soybean genome having at least 80%, 81%, 82%, 83%, 84%, 85%, 86%, 87%, 88%, 89%, 90%, 91%, 92%, 93%, 94%, 95%, 96%, 97%, 98%, 99% sequence identity to the nucleic acid sequence selected from the group consisting of SEQ ID NOs: 41, 43, 45, 47, 49, 51, 53, 55, 57, 59 and a combination thereof using nucleic acid primers comprising a nucleic acid sequence selected from the group consisting of SEQ ID NOs: 1, 2, 5, 6, 9, 10, 13, 14, 17, 18, 21, 22, 25, 26, 29, 30, 33, 34, 37, 38 and a combination thereof. In some aspects, the amplification step further includes the use of allele specific probes capable of hybridizing to a specific allele of the marker locus. For example, one or more probes comprising a nucleic acid sequence selected from the group consisting of SEQ ID NOs: 3, 4, 7, 8, 11, 12, 15, 16, 19, 20, 23, 24, 27, 28, 31, 32, 35, 36, 39, 40 and a combination thereof can be used in the present methods for detecting an allele of the marker loci associated with the desired or preferred reproductive growth phenotypes.

TABLE 3

Non-limiting list of suitable primers and probes for the detection of various marker loci of the present disclosure.

| Marker Locus | Linkage Group/ Chrom. No. | Relative Map Position (cM) | Approximate Physical Position of SNP (bp) | SEQ ID | Primer or Probe |
|---|---|---|---|---|---|
| F1 | G/18 | 103.23 | 60,914,550 | 1 | Primer |
|  |  |  |  | 2 | Primer |
|  |  |  |  | 3 | Allelic Probe |
|  |  |  |  | 4 | Allelic Probe |
| F2 | G/18 | 106.41 | 61,796,264 | 5 | Primer |
|  |  |  |  | 6 | Primer |
|  |  |  |  | 7 | Allelic Probe |
|  |  |  |  | 8 | Allelic Probe |
| F3 | G/18 | 102.65 | 60,840,873 | 9 | Primer |
|  |  |  |  | 10 | Primer |
|  |  |  |  | 11 | Allelic Probe |
|  |  |  |  | 12 | Allelic Probe |
| F4 | G/18 | 102.18 | 60,745,556 | 13 | Primer |
|  |  |  |  | 14 | Primer |
|  |  |  |  | 15 | Allelic Probe |
|  |  |  |  | 16 | Allelic Probe |
| F5 | G/18 | 106.86 | 61,963,221 | 17 | Primer |
|  |  |  |  | 18 | Primer |
|  |  |  |  | 19 | Allelic Probe |
|  |  |  |  | 20 | Allelic Probe |
| F6 | G/18 | 107.09 | 62,111,333 | 21 | Primer |
|  |  |  |  | 22 | Primer |
|  |  |  |  | 23 | Allelic Probe |
|  |  |  |  | 24 | Allelic Probe |
| F7 | G/18 | 106.82 | 61,948,911 | 25 | Primer |
|  |  |  |  | 26 | Primer |
|  |  |  |  | 27 | Allelic Probe |
|  |  |  |  | 28 | Allelic Probe |
| F8 | G/18 | 106.85 | 61,948,986 | 29 | Primer |
|  |  |  |  | 30 | Primer |
|  |  |  |  | 31 | Allelic Probe |
|  |  |  |  | 32 | Allelic Probe |
| M1 | G/18 | 96.76 | 59,884,959 | 33 | Primer |
|  |  |  |  | 34 | Primer |
|  |  |  |  | 35 | Allelic Probe |
|  |  |  |  | 36 | Allelic Probe |
| M2 | G/18 | 96.41 | 59,816,931 | 37 | Primer |
|  |  |  |  | 38 | Primer |
|  |  |  |  | 39 | Allelic Probe |
|  |  |  |  | 40 | Allelic Probe |

However, one of skill will immediately recognize that other primer and probe sequences could also be used. For instance, primers to either side of the given primers can be used in place of the given primers, so long as the primers can amplify a region that includes the allele to be detected, as can primers and probes directed to other marker loci. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the compositions and methods are not limited to the primers and probes specifically recited herein.

In certain embodiments, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Labeling strategies for labeling nucleic acids and their corresponding detection strategies can be found, e.g., in Haugland (1996) *Handbook of Fluorescent Probes and Research Chemicals Sixth Edition* by Molecular Probes, Inc. (Eugene, Oreg.); or Haugland (2001) *Handbook of Fluorescent Probes and Research Chemicals Eighth Edition* by Molecular Probes, Inc. (Eugene, Oreg.).

Detectable labels may also include reporter-quencher pairs, such as are employed in Molecular Beacon and TAQMAN® probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent. Generally, whether the quencher is fluorescent or simply releases the transferred energy from the reporter by nonradiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules,* 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland (2001) *Handbook of Fluorescent Probes and Research Chemicals Eighth Edition* by Molecular Probes, Inc. (Eugene, Oreg.), the content of which is incorporated herein by reference.

In certain embodiments, reporter-quencher pairs are selected from xanthene dyes including fluorescein and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters is the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other embodiments, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In one aspect, real time PCR or LCR is performed on the amplification mixtures described herein, e.g., using molecular beacons or TAQMAN® probes. A molecular beacon (MB) is an oligonucleotide that, under appropriate hybridization conditions, self-hybridizes to form a stem and loop structure. The MB has a label and a quencher at the termini of the oligonucleotide; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone et al. (1995) Nucl Acids Res 26:2150-2155; Tyagi & Kramer (1996) Nat Biotechnol 14:303-308; Blok & Kramer (1997) Mol Cell Probes 11:187-194; Hsuih et al. (1997) J Clin Microbiol 34:501-507; Kostrikis et al. (1998) Science 279:1228-1229; Sokol et al. (1998) Proc Natl Acad Sci USA 95:11538-11543; Tyagi et al. (1998) Nat Biotechnol 16:49-53; Bonnet et al. (1999) Proc Natl Acad Sci USA 96:6171-6176; Fang et al. (1999) J Am Chem Soc 121:2921-2922; Marras et al. (1999) Genet Anal Biomol Eng 14:151-156; and, Vet et al. (1999) Proc Natl Acad Sci USA 96:6394-6399. Additional details regarding MB construction and use are also found in the patent literature, e.g., U.S. Pat. Nos. 5,925,517; 6,150,097; and 6,037,130.

Another real-time detection method is the 5'-exonuclease detection method, also called the TAQMAN® assay, as set forth in U.S. Pat. Nos. 5,804,375; 5,538,848; 5,487,972; and 5,210,015, each of which is hereby incorporated by reference in its entirety. In the TAQMAN® assay, a modified probe, typically 10-30 nucleotides in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are typically attached to the probe within a few nucleotides of one another, usually within 30 nucleotides of one another, or within 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

One example of a suitable real-time detection technique that does not use a separate probe that binds intermediate to the two primers is the KASPar detection system/method, which is well known in the art. In KASPar, two allele specific primers are designed such that the 3' nucleotide of each primer hybridizes to the polymorphic base. For example, if the SNP is an A/C polymorphism, one of the primers would have an "A" in the 3' position, while the other primer would have a "C" in the 3' position. Each of these two allele specific primers also has a unique tail sequence on the 5' end of the primer. A common reverse primer is employed that amplifies in conjunction with either of the two allele specific primers. Two 5' fluor-labeled reporter oligos are also included in the reaction mix, one designed to interact with each of the unique tail sequences of the allele-specific primers. Lastly, one quencher oligo is included for each of the two reporter oligos, the quencher oligo being complementary to the reporter oligo and being able to quench the fluor signal when bound to the reporter oligo. During PCR, the allele-specific primers and reverse primers bind to complementary DNA, allowing amplification of the amplicon to take place. During a subsequent cycle, a complementary nucleic acid strand containing a sequence complementary to the unique tail sequence of the allele-specific primer is created. In a further cycle, the reporter oligo interacts with this complementary tail sequence, acting as a labeled primer. Thus, the product created from this cycle of PCR is a fluorescently-labeled nucleic acid strand. Because the label incorporated into this amplification product is specific to the allele specific primer that resulted in the amplification, detecting the specific fluor presenting a signal can be used to determine the SNP allele that was present in the sample.

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook; *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel"); and, *PCR Protocols A Guide to Methods and Applications* (Innis et al., eds) Academic Press Inc. San Diego, Calif. (1990) ("Innis"). Additional details regarding detection of nucleic acids in plants can also be found, e.g., in *Plant Molecular Biology* (1993) Croy (ed.) BIOS Scientific Publishers, Inc.

Other techniques for detecting SNPs can also be employed, such as allele specific hybridization (ASH) or nucleic acid sequencing techniques. ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Isolated polynucleotide or fragments thereof, e.g., a primers and/or probe, are capable of specifically hybridizing to other nucleic acid molecules under appropriate conditions. In some embodiments, the nucleic acid molecules comprise any of the marker loci of the present invention. It will be appreciated that suitable primers and probes to be used can be designed using any suitable method. It is not intended to be limited to any particular primer, primer pair or probe. For example, primers or probes can be designed using any suitable software program, such as LASERGENE® or Primer3. In one embodiment, the nucleic acid molecules comprise any of SEQ ID NOs: 1-60, complements thereof and fragments thereof. In another aspect, the nucleic acid molecules of the present invention include nucleic acid molecules that hybridize, for example, under high or low stringency, substantially homologous sequences, or that have both to these molecules. Conventional stringency conditions are described by Sambrook, and by Haymes et al. In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed. Appropriate stringency conditions that promote DNA hybridization are known to those skilled in the art or can be found in Current Protocols in Molecular Biology, John Wiley & Sons, N.Y., 1989, 6.3.1-6.3.6.

Typically, stringent conditions will be those in which the salt concentration is less than about 1.5 M Na ion, typically about 0.01 to about 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the thermal melting point (Tm) can be approximated from the equation of Meinkoth et al., *Anal. Biochem.* 138:267-284 (1984): Tm=81.5° C.+16.6 (log M) 4-0.41 (% GC)-0.61 (% form)-500/L; where M is the molarity of monovalent cations, % GC is the percentage of guano sine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm hybridization and/or wash conditions can be adjusted to hybridize to sequences of the desired identity. For example, if sequences with >90% identity are sought, the Tm can be decreased 10° C. Generally, stringent conditions are selected to be about 5° C. lower than Tm for the specific sequence and its complement at a defined ionic strength and pH. However, severely stringent conditions can utilize a hybridization and/or wash at 1, 2, 3, or 4° C. lower than the Tm; moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the Tm. Using the equation, hybridization and wash compositions, and desired Tm those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier, New York (1993); and Current Protocols in Molecular Biology, Chapter 2, Ausubel et al., Eds., Greene Publishing and Wiley-Inter-science, New York (1995). Hybridization and/or wash conditions can be applied for at least 10, 30, 60, 90, 120, or 240 minutes.

In some embodiments, a nucleic acid, e.g., primers and/or probes, of the present invention will specifically hybridize to one or more of the nucleic acid molecules set forth in SEQ ID NOs: 41, 43, 45, 47, 49, 51, 53, 55, 57 or 59 or complements thereof or fragments of either under moderately stringent conditions, for example at about 2.0×SSC and about 65° C. In an aspect, a nucleic acid of the present invention will specifically hybridize to one or more SEQ ID NOs: 41, 43, 45, 47, 49, 51, 53, 55, 57 or 59 or complements or fragments of either under high stringency conditions.

In some embodiments, a marker locus within or linked to a QTL associated with a preferred reproductive growth phenotype is localized within a genomic region comprising any one of SEQ ID NOs: 41-60. In other examples, a marker locus is localized within a genomic region having between 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any one of SEQ ID NOs: 41-60 or complements or fragments thereof. Unless otherwise stated, percent sequence identity is determined using the GAP program default parameters for nucleic acid alignment (Accelrys, San Diego, Calif., USA).

In some embodiments, a kit for detecting markers or haplotypes, and/or for correlating the markers or haplotypes with a desired phenotype (e.g., a preferred reproductive growth phenotype), are provided. Thus, a typical kit can include a set of marker probes and/or primers configured to detect at least one favorable allele of one or more marker locus within or linked to a QTL associated with a preferred reproductive growth phenotype. These probes or primers can be configured, for example, to detect the marker alleles noted in the tables and examples herein, e.g., using any available allele detection format, such as solid or liquid phase array based detection, microfluidic-based sample detection, etc. The kits can further include packaging materials for packaging the probes, primers, or instructions; controls, such as control amplification reactions that include probes, primers, and/or template nucleic acids for amplifications; molecular size markers; or the like.

System or kit instructions that describe how to use the system or kit and/or that correlate the presence or absence of the allele with the predicted preferred or non-preferred phenotype are also provided. For example, the instructions can include at least one look-up table that includes a correlation between the presence or absence of the favorable allele(s) and the predicted time to floral initiation. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector.

Isolated nucleic acids comprising a nucleic acid sequence coding for a preferred reproductive growth phenotype, or capable of detecting such a phenotypic trait, or sequences complementary thereto, are also included. In certain embodiments, the isolated nucleic acids are capable of hybridizing under stringent conditions to nucleic acids of a soybean cultivar phenotyped for a preferred reproductive growth phenotype, to detect marker loci associated with a preferred reproductive growth phenotype, including one or more of Satt472, BARC-048095-10484, BARC-038873-07372, A235_1, L002_2, Satt191, BARC-031343-07057, L154_1, Sat_117, H3_54HE_1, BARC-010491-00654, BARC-010495-00656, BARC-010497-00670, BARC-044741-08783, BARC-010255-00571, BARC-024251-04812, BARC-020069-04425, BARC-062677-18004, A690_2, Bng069_1, BARC-062769-18043, BARC-014799-01667, Sct_187, BARC-044363-08678, BARC-031121-06998, Sat_064, BARC-030123-06813, BARC-054735-12156, BARC-050577-09750, BARC-057845-14952, BARC-031193-07008, BARC-040605-07795, BARC-013647-01216, BARC-055537-13406, BARC-050575-09746, BARC-014379-01337, BARC-039397-07314, A378_1, Sat_372, BARC-043995-08576, L120_1, BARC-021603-04153, L183_1, BARC-039091-07442, BARC-039099-07444, A586_2, BARC-064703-18782, BARC-049989-09280, BARC-065273-19301, BARC-017669-03102, BARC-013305-00475, F1, F2, F3, F4, F5, F6, F7, F8, M1, M2 and any combination thereof. In such embodiments, the preferred reproductive growth phenotype may comprise early flowering or late flowering and/or early maturity, mid maturity or late maturity.

In a certain aspect, a kit for selecting at least one soybean plant by marker assisted selection of a QTL associated with days to initiation of flowering is provided, the kit comprising primers or probes for detecting a polymorphism in the soybean genome, wherein the physical location of the polymorphism is selected from the group consisting of 60/745,556 bp on chromosome 18, 60,840,873 bp on chromosome 18, 60,914,550 bp on chromosome 18, 61,796,264 bp on chromosome 18, 61,963,221 bp on chromosome 18, 62,111,333 bp on chromosome 18, 61,948,911 bp on chromosome 18, 61,948,986 bp on chromosome 18 and any combination thereof. In addition, instructions for using the primers or probes to detect the marker loci and correlate the marker loci with the predicted number of days from planting to the initiation of flowering is provided. In some embodiments, the primers or probes will comprise a detectable label, including, but not limited to, a FAM (6-carboxyfluorescein) or VIC (4,7,2'-trichloro-7'-phenyl-6-carboxyfluorescein) fluorophore at the 5' end.

In some embodiments, the primers or probes are selected from Table 3. For example, suitable primers or probes may comprise a nucleic acid sequence represented by any one of SEQ ID NOs: 1-32. Vectors comprising one or more of the nucleic acids represented by SEQ ID NOs: 1-59, expression products of such vectors expressed in a host compatible therewith, antibodies to the expression product (both polyclonal and monoclonal), and antisense nucleic acids are also included. In some embodiments, one or more of these nucleic acids is provided in a kit.

These systems and methods represent a wide variety of available detection methods which can be utilized to detect markers associated with a preferred or desired reproductive growth phenotype, but any suitable method could also be used.

Floral Development and Maturity

Discussed herein are days to initiation of flowering and days to maturity reproductive growth phenotypes. Soybean growth is often characterized as comprising two stages: vegetative growth and reproductive growth. The vegetative (V) stages are numbered according to how many fully-developed trifoliate leaves are present. The reproductive (R) stages begin at flowering and include pod development, seed development, and plant maturation. Soybean yield is impacted by genetics and environment, and various management practices can impact crop growth and yield in the context of the genetics of the crop. These stages are well-characterized and known (see, e.g., McWilliams et al. (1999) Soybean Growth & Management Quick Guide, A-1174, NDSU Extension Service), and summarized in the Table 4 below.

TABLE 4

Developmental Stages of the Soybean Plant

| Vegetative Stages | | Reproductive Stages |
|---|---|---|
| VE | Emergence | R1 | beginning bloom, 1$^{st}$ flower |
| VC | Cotyledon Stage | R2 | full bloom, flower in top 2 nodes |
| V1 | 1st trifoliate leaf | R3 | beginning pod, $^{3}/_{16}$" pod in top 4 nodes |
| V2 | 2$^{nd}$ trifoliate | R4 | full pod, $^{3}/_{4}$" pod in top 4 nodes |
| V3 | 3$^{rd}$ trifoliate | R5 | $^{1}/_{8}$" seed in top 4 nodes |
| Vn | nth trifoliate | R6 | full size seed in top 4 nodes |
| V6 | flowering should start soon | R7 | beginning maturity, one mature pod |
| | | R8 | full maturity, 95% of pods are mature |

As noted herein, soybean is a short-day crop and its development is largely determined by variety-specific day length requirements that initiate flowering. In other words, as the days grow shorter soybean will flower and enter into reproductive development stages. Due to this photoperiod requirement, days from planting until initiation of flowering (R1) or maturity (R8) cannot be accurately estimated for soybean due to variation in planting date and other environmental variations. After flowering, temperature drives development and the days until maturity can be estimated. The number of days from floral initiation (R1) until physiological maturity (R7) is usually independent of variety, but will vary slightly from year to year due to temperature differences between years. Although most sensitive to day length, soybean flowering will be delayed to some extent with later planting dates. However, later planted soybean initiates flowering during a warmer time of the year; therefore, post-flower development speeds up. The precise number of days from full flower (R2) until R7 cannot be predicted, but fairly reliable estimates can be derived from historical information (see, e.g., Holshouser (2010) "Days to Soybean Physiological Maturity," Virginia Cooperative Extension, Bulletin 3009-1459; and, Heatherly (2005) "Soybean maturity group, planting date and development related," Delta Farm Press, Oct. 14, 2005). Therefore, early flowering and late flowering phenotypes are scored in relation to other soybean plants in the same population. For example, a soybean plant comprising a marker allele favorable for early flowering will tend to initiate R1 earlier than a soybean plant comprising a marker allele favorable for late flowering when grown under the same conditions and in the same field.

A days to maturity phenotype is based upon the number of days from planting until maturity (R8). As with days to flowering, days to maturity of a given plant is typically measured in relation to other soybean plants in the same population and subject to the same growing conditions. For example, a soybean plant comprising a marker allele favorable for early maturity will tend to begin R8 earlier than a soybean plant comprising a marker allele favorable for late maturity when grown under the same conditions and in the same field. A soybean plant comprising a marker allele favorable for mid maturity will exhibit a shift to a later maturity date, but not to the extent of the late maturity phenotype. Furthermore, the magnitude of this shift varies depending on genetic background and environmental factors.

Therefore, detection of marker alleles favorable for the desired or preferred phenotypic trait in soybean plants and soybean germplasms can be used to select a soybean plant or soybean germplasm that is predicted to display the desired or preferred phenotypic trait(s). In some embodiments, the selected soybean plant displays a mean days to initiation of flowering that is different as compared non-selected soybean plant (i.e., a soybean plant in which the allele favorable for the preferred or desired days to initiation of flowering phenotype is not detected). In some embodiments, the methods provided herein are suitable for selecting a soybean plant that will display early flowering as compared to a non-selected plant (i.e., a soybean plant in which the allele favorable for early flowering is not detected). In such embodiments, the selected soybean plant displays a mean days to initiation of flowering that is at least 0.25-5 days earlier, or at least 0.25, 0.5, 0.75, 1, 1.25, 1.5, 1.75, 2, 2.25, 2.5, 2.75, 3, 4, 5, 6, 7, 8, 9, 10, 11, 12, 13, 14, 15, 16, 17, 18, 19, 20, 21, 22, 23, 24, 25, 26, 27, 28, 29, or more days earlier than the mean days to initiation of flowering of the non-selected soybean plant. In other embodiments, the selected soybean plant will display late flowering as compared to a non-selected plant (i.e., a soybean plant in which the allele favorable for early flowering is not detected). In such embodiments, the selected soybean plant displays a mean days to initiation of flowering that is at least 0.25-5 days later, or at least 0.25, 0.5, 0.75, 1, 1.25, 1.5, 1.75, 2, 2.25, 2.5, 2.75, 3, 4, 5, 6, 7, 8, 9, 10, 11, 12, 13, 14, 15, 16, 17, 18, 19, 20, 21, 22, 23, 24, 25, 26, 27, 28, 29, or more days later than the mean days to initiation of flowering of the non-selected soybean plant.

In some embodiments, the selected soybean plant displays a mean days to maturity that is different as compared non-selected soybean plant (i.e., a soybean plant in which the allele favorable for the preferred or desired days to maturity phenotype is not detected). In some embodiments, the methods provided herein are suitable for selecting a soybean plant that will display early maturity as compared to a non-selected plant (i.e., a soybean plant in which the allele favorable for early maturity is not detected). In such embodiments, the selected soybean plant displays a mean days to maturity that is at least 1-10 days earlier, or at least 0.25, 0.5, 0.75, 1, 1.25, 1.5, 1.75, 2, 2.25, 2.5, 2.75, 3, 4, 5, 6, 7, 8, 9, 10, 11, 12, 13, 14, 15, 16, 17, 18, 19, 20, 21, 22, 23, 24, 25, 26, 27, 28, 29, or more days earlier than the mean days to maturity of the non-selected soybean plant. In other embodiments, the selected soybean plant will display late maturity as compared to a non-selected plant (i.e., a soybean plant in which the allele favorable for late maturity is not detected). In such embodiments, the selected soybean plant displays a mean days to maturity that is at least 1-10 days later, or at least 0.25, 0.5, 0.75, 1, 1.25, 1.5, 1.75, 2, 2.25, 2.5, 2.75, 3, 4, 5, 6, 7, 8, 9, 10, 11, 12, 13, 14, 15, 16, 17, 18, 19, 20, 21, 22, 23, 24, 25, 26, 27, 28, 29, or more days later than the mean days to maturity of the non-selected soybean plant. In yet other embodiments, the selected soybean plant will display: early flowering and early maturity; early flowering and mid maturity; early flowering and late maturity; late flowering and early maturity; late flowering and mid maturity; or late flowering and late maturity.

MAS and Introgression

The use of marker assisted selection (MAS) to select a soybean plant or germplasm based upon detection of a particular marker, marker allele, polymorphism or haplotype of interest is provided. For instance, in certain embodiments, a soybean plant or germplasm possessing a certain predetermined favorable marker allele or haplotype will be selected via MAS. Using MAS, soybean plants or germplasm can be selected for markers or marker alleles that positively correlate with a desired or preferred reproductive growth phenotype, without actually raising soybean and measuring for tolerance (or, contrawise, soybean plants can be selected against if they possess markers that negatively correlate with a desired or preferred reproductive growth phenotype). MAS is a powerful tool to select for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some aspects, the information disclosed herein regarding marker loci, marker alleles, haplotypes and/or marker profiles can be used to aid in the creation and/or selection of soybean plants, soybean germplasms, soybean breeding plants, lines, and populations for a preferred reproductive growth phenotype, including: (1) early flowering; (2) late flowering; (3) early flowering and early maturity, mid maturity, or late maturity; (4) late flowering and early maturity, mid maturity, or late maturity; (5) an extended reproductive growth stage; or (6) an optimized or maximized length of reproductive growth.

Further, the marker loci, marker alleles, haplotypes, QTLs and/or marker profiles described herein can be used for introgression into elite soybean germplasm, exotic soybean germplasm, or any other soybean germplasm. In some embodiments, the marker loci, marker alleles, haplotypes, QTLs and/or marker profiles can be used to aid in the creation and/or selection of breeding plants, lines, and populations for a preferred reproductive growth phenotype for a specific area of adaptation or target environment. Also provided is a method for introgressing into a soybean germplasm a soybean QTL, marker, marker allele, haplotype, and/or marker profile associated with at least one desired or preferred reproductive growth trait, including: (1) early flowering; (2) late flowering; (3) early maturity; (4) mid maturity (5) late maturity; (6) late flowering and early maturity; (7) late flowering and mid maturity; (8) late flowering and late maturity; (9) early flowering and early maturity; (10) early flowering and mid maturity; (11) early flowering and late maturity; (12) an extended reproductive growth stage; or (13) an optimized or maximized length of reproductive growth. Plants so created and selected can be used in a soybean breeding program. Through the process of introgression, the QTL, marker, marker allele, haplotype, and/or marker profile associated with a preferred time or length of at least one reproductive growth stage is introduced from plants identified using marker-assisted selection (MAS) to other plants, such as recurrent parental lines. According to the method, agronomically desirable plants and seeds can be produced containing the QTL, marker, marker allele, haplotype, and/or marker profile associated with a preferred reproductive growth phenotype from germplasm containing the QTL, marker, haplotype, and/or marker profile.

Also provided herein is a method for producing a soybean plant adapted for a desired or preferred reproductive growth phenotype. In certain aspects, a soybean plant or soybean germplasm is first identified and/or selected for a desired or preferred reproductive growth phenotype by detecting one or more marker loci or marker alleles via MAS as explained herein. In such aspects, the desired or preferred reproductive growth phenotype comprises one or more of: (1) early flowering; (2) late flowering; (3) early maturity; (4) mid maturity (5) late maturity; (6) late flowering and early maturity; (7) late flowering and mid maturity; (8) late flowering and late maturity; (9) early flowering and early maturity; (10) early flowering and mid maturity; (11) early flowering and late maturity; (12) an extended reproductive growth stage; or (13) an optimized or maximized length of reproductive growth. The selected soybean plant or soybean germplasm can then be used as a donor soybean plant in a breeding program. Selected soybean plant material may represent, among others, an inbred line, a hybrid line, a heterogeneous population of soybean plants, or an individual plant. According to techniques well known in the art of plant breeding, this donor parental line is crossed with a second parental line. In some embodiments, the second parental line is a recurrent parental plant, such as a high yielding line. This cross produces a segregating plant population composed of genetically heterogeneous plants. Plants of the segregating plant population are screened for the QTL, marker, marker allele, or haplotype associated with the desired or preferred reproductive growth phenotype, and a subpopulation of the segregating plant population that contains the QTL, marker, marker allele, or haplotype associated with the desired or preferred reproductive phenotype is selected. Further breeding may include, among other techniques, additional crosses with other lines, hybrids, backcrossing, or self-crossing. The result is a line of soybean plants that has a preferred reproductive growth phenotype and optionally also has other desirable traits from one or more other soybean lines.

In some embodiments, a soybean plant or soybean germplasm comprising one or more marker loci, marker alleles, haplotypes, marker profiles or QTLs associated with one or more reproductive growth phenotypes using the methods described herein is crossed with a recurrent soybean parent to produce a population of progeny soybean germplasm, wherein one or more marker loci, marker alleles, haplotypes, marker profiles or QTLs associated with the reproductive growth phenotype(s), e.g., days to initiation of flowering and/or days to maturity, is introgressed into a subpopulation of soybean progeny germplasm. The resulting soybean progeny plants or soybean progeny germplasms containing the one or more marker loci, marker alleles, haplotypes, marker profiles or QTLs of interest can then be identified and selected using the methods described herein. In certain embodiments, a progeny soybean plant grown from the subpopulation of progeny soybean germplasm displays an altered reproductive growth phenotype as compared to the recurrent soybean parent, such as:

(i) increased number of days from planting to initiation of flowering;

(ii) decreased number of days from planting to initiation of flowering;

(iii) decreased number of days from planting to maturity;

(iv) increased number of days from planting to maturity;

(v) decreased number of days from planting to initiation of flowering and decreased number of days from planting to maturity;

(vi) decreased number of days from planting to initiation of flowering and increased number of days from planting to maturity;

(vii) increased number of days from planting to initiation of flowering and the same average number of days from planting to maturity; or (vii) decreased number of days from planting to initiation of flowering and the same average number of days from planting to maturity.

In other embodiments, a progeny soybean plant grown from the subpopulation of progeny soybean germplasm displays an altered reproductive growth phenotype compared to other plants grown in the field that do not contain the one or more marker loci, marker alleles, haplotypes, marker profiles, or QTLs of interest. The progeny soybean plant may exhibit:

(i) increased number of days from planting to initiation of flowering as compared to a soybean plant not comprising the allele of at least one marker locus linked to the QTL associated with days to initiation of flowering;

(ii) decreased number of days from planting to initiation of flowering as compared to a soybean plant not comprising the allele of at least one marker locus linked to the QTL associated with days to initiation of flowering;

(iii) decreased number of days from planting to maturity as compared to a soybean plant not comprising the allele of at least one marker locus linked to the QTL associated with days to maturity;

(iv) increased number of days from planting to maturity as compared to a soybean plant not comprising the allele of at least one marker locus linked to the QTL associated with days to maturity;

(v) decreased number of days from planting to initiation of flowering and decreased number of days from planting to maturity as compared to a soybean plant not comprising the allele of at least one marker locus linked to the QTL associated with days to initiation of flowering or the allele of at least one marker locus linked to the QTL associated with days to maturity; or (vi) decreased number of days from planting to initiation of flowering and increased number of days from planting to maturity as compared to a soybean plant not comprising the allele of at least one marker locus linked to the QTL associated with days to initiation of flowering or the allele of at least one marker locus linked to the QTL associated with days to maturity.

In some embodiments, the soybean progeny plant displays early flowering as compared to other soybean plants in the field or the recurrent parent (i.e., a soybean plant in which the allele favorable for early flowering is not detected). In such embodiments, the soybean progeny plant displays a mean days to initiation of flowering that is at least 0.25-5 days earlier, or at least 0.25, 0.5, 0.75, 1, 1.25, 1.5, 1.75, 2, 2.25, 2.5, 2.75, 3, 4, 5, 6, 7, 8, 9, 10, 11, 12, 13, 14, 15, 16, 17, 18, 19, 20, 21, 22, 23, 24, 25, 26, 27, 28, 29, or more days earlier than the mean days to initiation of flowering of the other soybean plants in the field or the recurrent parent. In other embodiments, the soybean progeny plant will display late flowering as compared to other soybean plants in the field or the recurrent parent (i.e., a soybean plant in which the allele favorable for early flowering is not detected). In such embodiments, the soybean progeny plant displays a mean days to initiation of flowering that is at least 0.25-5 days later, or at least 0.25, 0.5, 0.75, 1, 1.25, 1.5, 1.75, 2, 2.25, 2.5, 2.75, 3, 4, 5, 6, 7, 8, 9, 10, 11, 12, 13, 14, 15, 16, 17, 18, 19, 20, 21, 22, 23, 24, 25, 26, 27, 28, 29, or more days later than the mean days to initiation of flowering of the other soybean plants in the field or the recurrent parent.

In some embodiments, the soybean progeny plant displays early maturity as compared to other soybean plants in the field or the recurrent parent (i.e., a soybean plant in which the allele favorable for early maturity is not detected). In such embodiments, the soybean progeny plant displays a mean days to maturity that is at least 1-10 days earlier, or at least 0.25, 0.5, 0.75, 1, 1.25, 1.5, 1.75, 2, 2.25, 2.5, 2.75, 3, 4, 5, 6, 7, 8, 9, 10, 11, 12, 13, 14, 15, 16, 17, 18, 19, 20, 21, 22, 23, 24, 25, 26, 27, 28, 29, or more days earlier than the mean days to maturity of other soybean plants in the field or the recurrent parent. In other embodiments, the soybean progeny plant will display late maturity as compared to other soybean plants in the field or the recurrent parent (i.e., a soybean plant in which the allele favorable for late maturity is not detected). In such embodiments, the soybean progeny plant displays a mean days to maturity that is at least 1-10 days later, or at least 0.25, 0.5, 0.75, 1, 1.25, 1.5, 1.75, 2, 2.25, 2.5, 2.75, 3, 4, 5, 6, 7, 8, 9, 10, 11, 12, 13, 14, 15, 16, 17, 18, 19, 20, 21, 22, 23, 24, 25, 26, 27, 28, 29, or more days later than the mean days to maturity of the other soybean plants in the field or the recurrent parent.

In some embodiments, one parent is adapted for a northern growing region, and the second parent is not adapted for a northern growing region. In some embodiments, the parent adapted for a northern growing region comprises a better reproductive growth phenotype for a northern growing region than the parent not adapted for a northern growing region. In some embodiments, the method further comprises obtaining progeny better adapted for a northern growing region.

In some embodiments, the methods include identifying trait loci in a mixed defined plant population comprising multiple plant families (see, e.g., U.S. Pat. No. 6,399,855, herein incorporated by reference in its entirety). The method comprises quantifying a phenotypic trait across lines sampled from the population, identifying at least one genetic marker associated with the phenotypic trait by screening a set of markers and identifying the quantitative trait loci based on the association of the phenotypic trait and the genetic marker(s). In some embodiments, the plant population consists of diploid plants, either hybrid or inbred. The phenotypic traits associated with the locus are quantitative such that a numerical value can be ascribed to the trait, and the association of the genetic loci and the phenotypic trait is determined through specified statistical models. In some embodiments, the statistical models are linear models with fixed effects and random effects. In a other embodiments, the statistical model is a mixed effects model.

Soybean plants, germplasms seeds, tissue cultures, variants and mutants having a preferred reproductive growth phenotype produced by the foregoing methods are also provided. Soybean plants, seeds, tissue cultures, variants and mutants comprising one or more of the marker loci, one or more of the favorable alleles, and/or one or more of the haplotypes and having a preferred reproductive growth phenotype are provided. Also provided are isolated nucleic acids, kits, and systems useful for the identification, prediction, and/or selection methods disclosed herein.

In some embodiments, the soybean plant, germplasm, plant part, or seed having a preferred reproductive growth phenotype further comprises one or more other traits of interest including but not limited to improved resistance to one or more ALS-inhibiting herbicides, a hydroxyphenylpyruvatedioxygenase inhibitor, a phosphanoglycine (including but not limited to a glyphosate), a sulfonamide, an imidazolinone, a bialaphos, a phosphinothricin, a metribuzin, a mesotrione, an isoxaflutole, an azafenidin, a butafenacil, a sulfosate, a glufosinate, a dicamba, a 2,4-D, and a protox inhibitor. In some embodiments, resistance to the herbicidal formulation is conferred by a transgene. In some embodiments, the plant or germplasm further comprises a trait selected from the group consisting of drought tolerance, stress tolerance, disease resistance, herbicide resistance, enhanced yield, modified oil, modified protein, tolerance to chlorotic conditions, insect resistance and any combination thereof. In some embodiments, the trait is selected from the group consisting of brown stem rot resistance, charcoal rot drought complex resistance, *Fusarium* resistance, *Phytophthora* resistance, stem canker resistance, sudden death syndrome resistance, *Sclerotinia* resistance, *Cercospora* resistance, anthracnose resistance, target spot resistance, frogeye leaf spot resistance, soybean cyst nematode resistance, root knot nematode resistance, rust resistance, high oleic content, low linolenic content, aphid resistance, stink bug resistance, iron chlorosis deficiency tolerance and any combination thereof. In some embodiments, one or more of the traits is conferred by one or more transgenes, by one or more native loci, or any combination thereof.

The present disclosure is illustrated by the following examples. The foregoing and following description and the various examples are not intended to be limiting but rather are illustrative of the described embodiments. Hence, it will be understood that the present disclosure is not limited to the specific details of these examples.

EXAMPLES

Example 1. Days to Initiation of Flowering QTL Mapping

Crosses were made between soybean varieties differing in flowering time. F1 individuals were self-fertilized to the F3:4 or F4:5 generation (Table 5). The average number of days from planting to R1 across an F3:4 or F4:5 progeny line was used as the days to initiation of flowering phenotype. The populations were planted in environments concordant with their expected maturities.

Leaf discs from eight F3:4 or F4:5 plants were pooled per family. Genomic DNA was extracted from leaf tissue of each progeny using a modification of the CTAB (cetyltriethylammonium bromide, Sigma H5882) method described by Stacey & Isaac (Methods in Molecular Biology, Vol. 28: Protocols for Nucleic Acid Analysis by Nonradioactive Probes, Ed: Isaac, Humana Press Inc, Totowa, N.J. 1994, Ch 2, pp. 9-15). Approximately 100-200 mg of tissue was ground into powder in liquid nitrogen and homogenized in 1 ml of CTAB extraction buffer (2% CTAB, 0.02 M EDTA, 0.1 M Tris-Cl pH 8, 1.4 M NaCl, 25 mM DTT) for 30 minutes at 65° C. Homogenized samples were cooled at room temperature for 15 minutes before a single protein extraction with approximately 1 ml 24:1 v/v chloroform:octanol was done. Samples were centrifuged for 7 min at 13,000 rpm and the upper layer of supernatant was collected using wide-mouthed pipette tips. DNA was then precipitated from the supernatant by incubation in 95% ethanol on ice for 1 hour. DNA threads were spooled onto a glass hook, washed in 75% ethanol containing 0.2 M sodium acetate for 10 minutes, air-dried for 5 minutes and resuspended in TE buffer. Five μl RNAse A was added to the samples and incubated at 37° C. for 1 hour.

An average of 140 polymorphic TaqMan SNP assays approximately evenly spaced across the soy genome were used to genotype the bulk samples.

Multiple QTL mapping analysis (MQM) was performed using the MQM R/QTL package under recommended parameters as described in, e.g., Broman, K. W. and Sen, S., A guide to QTL mapping with R/qtl. Springer. http://www.rqtl.org/book (2009); Arends, D. et al., R/qtl: high-throughput multiple QTL mapping, *Bioinformatics* 26(23): 2990-2992 (2010); and Arends, D. et al., Tutorial-Multiple-QTL Mapping (MQM) Analysis for R/qt, http://www.rqtl.org/tutorials/MQM-tour.pdf (2014).

As shown in Table 5, QTL mapping within eight bi-parental populations grown across multiple environments reveal a region on chromosome 18 of soybean between ~94.3 cM and 107.1 cM (~59,472,481 bp and 62,259,025 bp) that is associated with days to initiation of flowering variation. The bi-parental populations are identified by the parental soybean variety (i.e., V10-V140) used in the cross. The LOD value of 3.0 or higher is considered evidence of linkage. The variance in each population explained by the QTL ranged from 5.08% to 22.52%. While the average peak of the QTL effect occurs at 103.5 cM, the paucity of genotyped markers flanking the QTL and limited population sizes could impact accurate estimation of the true QTL peak position. The additive effect of the QTL on days to R1 ranged from 0.5-2 days depending on the population and environment, suggesting that the QTL has a large impact on flowering time. The additive effect is provided in positive and negative values. An additive effect with a negative value indicates that the female parent displayed the later flowering time as compared to the progeny population, whereas an additive effect with a positive value indicates that the male parent displayed the later flowering time as compared to the progeny population.

TABLE 5

Days to Initiation of Flowering QTL Mapping Results

| PopName ♀ × ♂ | Location | LOD | VAR | QTLPeak | Additive Effect | Parent giving late Effect | Peak Marker |
|---|---|---|---|---|---|---|---|
| V10 × V20 | 1 | 5.29 | 16.63 | 103.2 | −0.91 | V10 | F1 |
| V30 × V40 | 2 | 6.35 | 17.73 | 102.7 | −0.76 | V30 | F3 |
| V50 × V60 | 2 | 5.21 | 5.08 | 102.2 | 1.54 | V60 | F4 |
| V70 × V80 | 3 | 8.60 | 20.89 | 106.4 | −0.56 | V70 | F2 |
| V90 × V100 | 4 | 8.42 | 16.15 | 106.4 | 1.23 | V100 | F2 |
| V90 × V100 | 5 | 7.75 | 14.37 | 106.4 | 0.74 | V100 | F2 |
| V90 × V100 | 3 | 11.53 | 16.73 | 106.4 | 1.67 | V100 | F2 |
| V110 × V120 | 6 | 25.10 | 22.52 | 106.4 | 2.13 | V120 | F2 |
| V130 × V30 | 1 | 5.94 | 7.72 | 103.2 | 0.63 | V30 | F1 |
| V140 × V30 | 7 | 4.84 | 8.66 | 103.2 | 0.86 | V30 | F1 |

PopName = the population produced by the breeding pair
LOD = logarithm (base10) of odds
Var = percent variance

Example 2. Days to Initiation of Flowering Haplotype Analysis

DNA libraries were prepared from DNA extracted from the parents of the populations as in Example 1 using standard Illumina TruSeq-V3 chemistry (Illumina.com), and whole-genome shotgun sequencing was performed using the Illumina Hi-Seq 2000. Samples were sequenced to ~3-5× coverage (3-5 Gb/DNA library). Paired-end 101 bp sequencing reads were obtained and used for SNP calling and genotyping. For SNP calling, reads were aligned against the Glyma1v1.1 assembly (Schmutz et al. 2010) using Bowtie2 (Langmead and Salzberg 2012), and SNPs were called from unique alignments at a coverage of 3 and purity of 0.98. SNPs occurring within 45 Kb windows and spanning the region between 61,650,000 and 62,307,395 bp of soybean chromosome 18 were used to identify haplotype blocks. Two lines were considered to have the same haplotype block if within a 45 Kb window 95% or greater of the SNP genotypes matched. A minimum of three SNPs were required to determine a haplotype.

Figure 2:
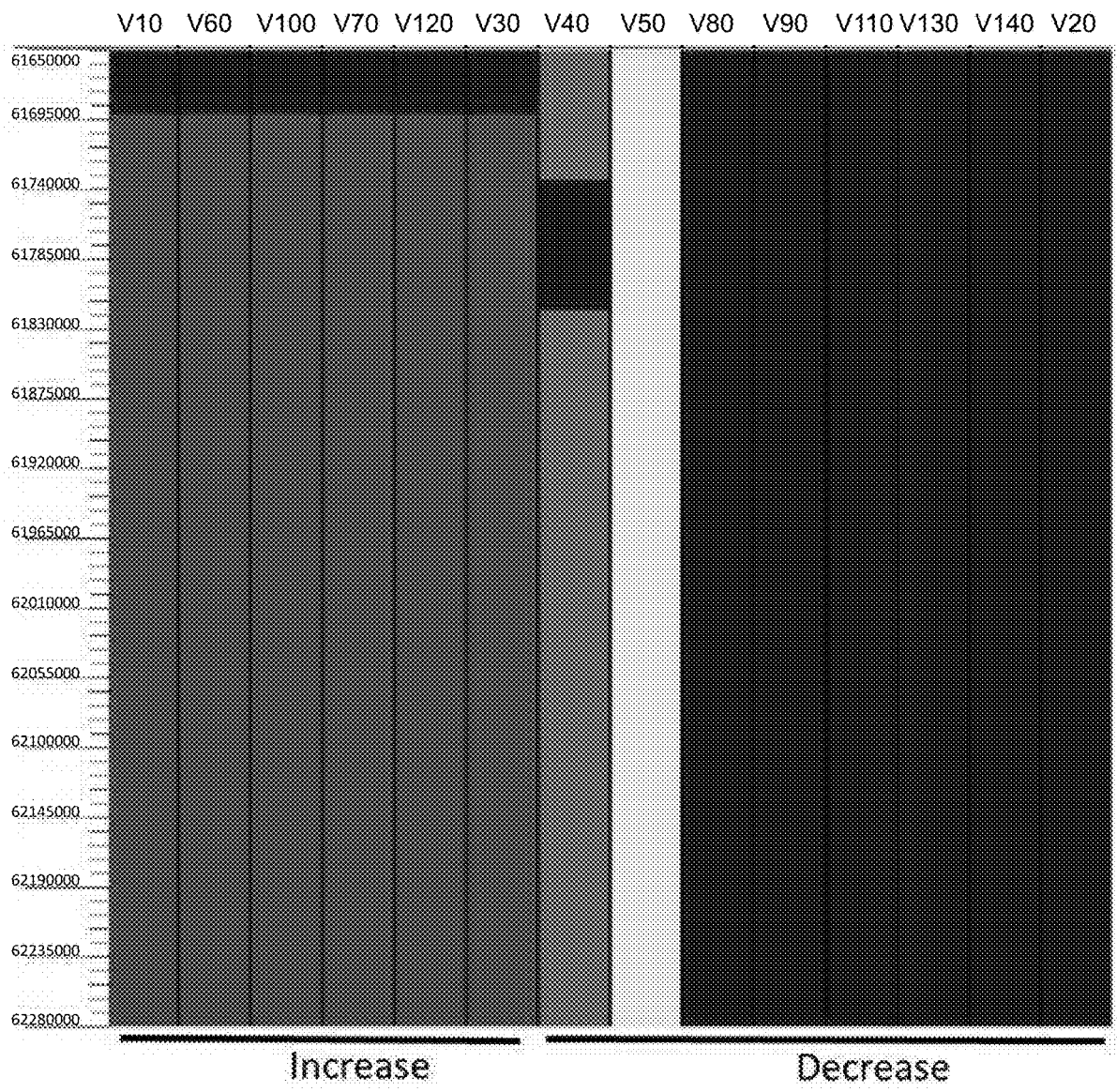
FIG. 2 is a chart representing the fine-mapping of the QTL region on chromosome 18. The y-axis shows the physical position of the QTL and surrounding chromosomal region provided in base pairs (bp) on chromosome 18. The physical positions are based on the *Glycine max* Williams 82 V1.1 genome sequence described in Schmutz et al., "Genome sequence of the palaeopolyploid soybean" (2010) Nature 463:178-183, and is also available at the GenBank website (http://www.ncbi.nlm.nih.gov/). The "increase" in time from planting to initiation of flowering is indicated on the left side of the x-axis, whereas the "decrease" from time from planting to initiation of flowering is indicated on the right side of the x-axis. Soybean varieties are indicated at the top of the chart. The colors represent contrasting haplotypes across 45 kilobase (kb) intervals. The blue, pink, and yellow haplotypes are associated with decrease in flowering time, and the red haplotype is associated with an increase in flowering time.

High-density genotyping following re-sequencing revealed that between 99.3-106.2 cM, the V70, V110, V120, V90, V100, V130, V140, V20, V80 soybean varieties are identical-in-state suggesting that the QTL is located in the region of genetic contrast between 106.4 and 107.1 cM (61/695,000 and 62,307,395 bp). FIG. 2 shows additional analysis in this interval, which revealed haplotypes associated with days to initiation of flowering variation. The colors represent contrasting haplotypes across 45 Kb intervals. The blue, pink, and yellow haplotypes are associated with decrease in days to initiation of flowering and the red haplotype is associated with an increase in days to initiation of flowering. Within this fine-mapped QTL region, 142 SNPs were identified that perfectly distinguished the parental soybean varieties associated with late or early responses to flowering time.

Making new crosses between parents with contrasting late effect and early effect haplotypes would potentially produce a population segregating for days to initiation of flowering and selection of the associated haplotype could skew a population towards a desired flowering time.

Example 3. Days to Maturity QTL Mapping

Crosses were made between soybean varieties differing in maturity time. F1 individuals were self-fertilized to the F3:4 or F4:5 generation (Table 6). The average number of days from planting to maturity across an F3:4 or F4:5 progeny line was used as the days to days to maturity phenotype. The populations were planted in environments concordant with their expected maturities.

Leaf discs from eight F3:4 or F4:5 plants were pooled per family. Genomic DNA was extracted from leaf tissue of each progeny using a modification of the CTAB as described elsewhere herein. Multiple QTL mapping analysis (MQM) was performed using the MQM R/QTL package under recommended parameters as described elsewhere herein.

As shown in Table 6, QTL mapping within nineteen bi-parental populations grown across multiple environments reveal a region on chromosome 18 of soybean between ~89 cM and 102 cM that is associated with days to maturity variation. The bi-parental populations are identified by the parental soybean variety used in the cross. The variance in each population explained by the QTL ranged from 3.53% to 24.12%. The average peak of the QTL effect occurs at approximately 96 cM. The additive effect of the QTL on days to maturity ranged from 0.2-1.6 days depending on the population and environment, suggesting that the QTL has a large impact on days to maturity.

TABLE 6

Days to Maturity QTL Mapping Results

| PopName ♀ × ♂ | LOC | LOD | VAR | QTLPeak | Additive Effect | Parent Giving Late Effect |
|---|---|---|---|---|---|---|
| V150 × V290 | 8 | 8.800973 | 6.699806 | 89.01 | −1.37721 | V150 |
| V150 × V290 | 9 | 5.728749 | 4.03764 | 80.31 | −0.6536 | V150 |
| V30 × V40 | 2 | 6.817261 | 17.30092 | 95.03 | −1.47084 | V30 |
| V160 × V300 | 10 | 6.130099 | 5.517253 | 94.16 | −1.18906 | V160 |
| V170 × V310 | 4 | 3.257543 | 7.506793 | 96.86 | 0.632611 | V310 |
| V180 × V320 | 10 | 3.459863 | 8.847405 | 91.27 | −0.71011 | V180 |
| V190 × V330 | 9 | 6.497489 | 5.18818 | 95.03 | −1.33613 | V190 |
| V200 × V170 | 11 | 5.653343 | 12.9759 | 96.86 | −1.05119 | V200 |
| V200 × V320 | 4 | 5.2 | 5.91 | 91.63 | −0.58 | V200 |
| V80 × V320 | 12 | 12.20201 | 14.41989 | 99.25 | −1.05721 | V80 |
| V80 × V320 | 11 | 4.940921 | 6.449379 | 96.5 | −0.7058 | V80 |
| V80 × V320 | 4 | 16.27096 | 15.84922 | 96.5 | −1.03789 | V80 |
| V80 × V320 | 3 | 3.475575 | 8.787827 | 99.25 | −0.54174 | V80 |
| V210 × V320 | 4 | 6.33 | 8.43 | 102.61 | −0.51 | V210 |
| V90 × V340 | 13 | 4.43248 | 6.672591 | 82.29 | −1.446 | V90 |
| V110 × V340 | 5 | 9.086881 | 18.4907 | 101.08 | −1.32272 | V110 |
| V220 × V350 | 14 | 3.943594 | 3.538194 | 94.28 | 0.781909 | V350 |
| V140 × V370 | 7 | 8.255718 | 20.00235 | 96.5 | −1.56257 | V140 |
| V240 × V80 | 10 | 5.348546 | 14.72817 | 91.27 | 1.457109 | V80 |
| V240 × V80 | 12 | 5.816055 | 24.12803 | 77.28 | 1.381696 | V80 |
| V240 × V380 | 10 | 4.092565 | 12.18035 | 86.73 | 1.022389 | V380 |
| V260 × V320 | 10 | 3.966617 | 8.029377 | 81.45 | −0.9916 | V260 |
| V270 × V320 | 10 | 5.929789 | 6.940837 | 87.25 | −0.90099 | V270 |
| V270 × V320 | 4 | 4.179158 | 4.52239 | 87.25 | −0.38378 | V270 |
| V280 × V230 | 16 | 3.897709 | 5.646795 | 93.61 | −0.42514 | V280 |
| V280 × V230 | 17 | 4.562878 | 8.357237 | 93.61 | −0.20546 | V280 |

PopName = the population produced by the breeding pair
LOD = logarithm (base10) of odds
Var = percent variance

Example 4. Exemplary SNP Detection Assays

From the analyses of marker loci associated with days to initiation of flowering in soybean populations and varieties, several markers were developed, tested, and confirmed. Genotyping assays were developed to two SNPs that perfectly distinguished haplotypes with an early or late flowering phenotype. Using one or both of these assays enable marker assisted selection. Any methodology can be deployed to use this information, including but not limited to, any one or more of sequencing or marker methods.

For example, sample tissue, including tissue from soybean leaves or seeds can be extracted from leaf discs using, e.g., a modification of the CTAB method described in Example 1, and screened with the markers using a TAQMAN® PCR assay system (Life Technologies, Grand Island, N.Y., USA).

Exemplary TAQMAN® Assay Conditions
Reaction Mixture (Total Volume=5 µl):

| | |
|---|---|
| Genomic DNA (dried) | 16 ng |
| DDH2O | 2.42 µl |
| Klearkall Mastermix | 2.5 µl |
| Forward primer (100 µM) | 0.0375 µl |
| Reverse primer (100 µM) | 0.0375 µl |
| Probe 1 (100 µM) | 0.005 µl |
| Probe 2 (100 µM) | 0.005 µl |

Reaction Conditions:

| | |
|---|---|
| 94° C. | 10 min 1 cycle |

40 cycles of the following:

| | |
|---|---|
| 94° C. | 30 sec |
| 60° C. | 60 sec |

Klearkall Mastermix is available from KBioscience Ltd. (Hoddesdon, UK).

Primers and probes suitable for the detection of these SNPs are provided in Table 3. The haplotypes associated with an early or late flowering effect for eight parental soybean varieties are shown in Tables 7 and 8.

TABLE 7

| Marker | Approx. Physical position (bp) | Late Flowering allele | Early Flowering allele | Soybean Variety Displaying Increased Flowering Time | | | | | |
|---|---|---|---|---|---|---|---|---|---|
| | | | | V10 | V30 | V60 | V100 | V70 | V120 |
| F2 | 61,796,264 | A | T | A | A | A | A | A | A |
| F6 | 62,111,333 | G | A | G | G | G | G | G | G |

TABLE 8

| Marker | Approx. Physical position (bp) | Late Flowering allele | Early Flowering allele | Soybean Variety Displaying Decreased Flowering Time | | | | | | | |
|---|---|---|---|---|---|---|---|---|---|---|---|
| | | | | V80 | V90 | V110 | V130 | V140 | V20 | V50 | V40 |
| F2 | 61,796,264 | A | T | T | T | T | T | T | T | T | T |
| F6 | 62,111,333 | G | A | A | A | A | A | A | A | A | A |

In addition, three candidate functional variants were identified and that can be used to distinguished haplotypes associated with an early or late flowering phenotype. One SNP (F5) was identified within the Flowering Locus T homolog, ft1b, and two SNPs (F7 and F8) were identified within the Flowering Locus T homolog, ft1a. These SNPs putatively confer changes to the encoded protein and are associated with either an increase or decrease in days to initiation of flowering. Primers and probes suitable for the detection of these SNPs are provided in Table 3. The haplotypes associated with an early or late flowering effect for eight parental soybean varieties are shown in Tables 9 and 10.

TABLE 9

| Marker | Approx. Physical position (bp) | Late Flowering allele | Early Flowering allele | Soybean Variety Displaying Increased Flowering Time | | | | | |
|---|---|---|---|---|---|---|---|---|---|
| | | | | V10 | V30 | V60 | V100 | V70 | V120 |
| F7 | 61,948,911 | C | G | | | C | C | C | C |
| F8 | 61,948,986 | A | G | A | | A | | A | A |
| F5 | 61,963,221 | C | A | C | | | | C | C |

TABLE 10

| Marker | Approx. Physical position (bp) | Late Flowering allele | Early Flowering allele | Soybean Variety Displaying Decreased Flowering Time | | | | | | | |
|---|---|---|---|---|---|---|---|---|---|---|---|
| | | | | V80 | V90 | V110 | V130 | V140 | V20 | V50 | V40 |
| F7 | 61,948,911 | C | G | G | G | G | | G | G | G | G |
| F8 | 61,948,986 | A | G | G | G | G | G | G | G | | G |
| F5 | 61,963,221 | C | A | | | A | A | A | A | A | A |

Example 5. SNP Analysis for Days to Initiation of Flowering Across a Diverse Population of Elite Soybean Breeding Lines A diverse population of inbred elite soybean lines were genotyped at marker locus F5 to determine the effect of the QTL associated with days to initiation of flowering. Fifty-five different inbred elite breeding lines in maturity group 2 and eighty-five different inbred elite breeding lines in maturity group 3 were phenotyped for days to initiation of flowering during the growing season. Plots for each breeding line were examined every two to three days and checked for flowering. The initiation of flowering for each plot was recorded when 50% of the plants in the plot had one flower anywhere on the plant. The number of days from planting to flowering was recorded. Plants from each elite breeding line were leaf punched and genotyped at marker locus F5 using DNA extraction and SNP detection techniques described elsewhere herein. Within each maturity group, elite breeding lines containing the early flowering allele of marker locus F5 displayed a mean days to initiation of flowering that was reduced compared to elite breeding lines containing the late flowering allele of marker locus F5. The data is summarized in Table 11.

TABLE 11

Days to initiation of flowering phenotype summary data.

| Marker | Maturity Group 2 | | Maturity Group 3 | |
|---|---|---|---|---|
| Locus F5 Allele | Mean Days to Flowering | Number of Elite Breeding Lines | Mean Days to Flowering | Number of Elite Breeding Lines |
| A | 52.9 | 43 | 50.3 | 77 |
| C | 53.5 | 12 | 51.2 | 8 |

That which is claimed:

1. A method of selecting a soybean plant or soybean germplasm with one or more reproductive growth phenotypes, the method comprising:
   (a) isolating nucleic acids from a genome of a first soybean plant or soybean germplasm;
   (b) detecting in the first soybean plant or first soybean germplasm at least one allele of marker locus F5 on chromosome 18 favorable for a first reproductive growth phenotype selected from the group consisting of early flowering and late flowering, wherein the at least one allele favorable for early flowering is allele A at marker locus F5 on chromosome 18 and the at least one favorable allele for late flowering is allele C at marker locus F5 on chromosome 18;
   (c) selecting the first soybean plant or first soybean germplasm comprising the at least one allele from step (b), thereby selecting a soybean plant with a first reproductive growth phenotype selected from the group consisting of early flowering and late flowering; and
   (d) crossing the selected first soybean plant or soybean germplasm with a second soybean plant or soybean germplasm, thus producing a soybean plant or soybean germplasm with a marker profile associated with the first reproductive growth phenotype.

2. The method of claim 1, wherein the first reproductive growth phenotype is early flowering.

3. The method of claim 2, wherein the detecting step further comprises detection of at least one additional marker allele selected from the group consisting of allele T at marker locus F2, allele A at marker locus F6, allele G at marker locus F7, allele G at marker locus F8, or a combination thereof.

4. The method of any one of claims 1, 2 and 3, wherein detecting comprises sequencing at least one of the marker loci.

5. The method of any one of claims 1, 2 and 3, wherein detecting comprises amplifying a nucleic acid sequence comprising the marker locus of each said allele and detecting the resulting amplified nucleic acid comprising each marker locus.

6. The method of claim 5, wherein the amplifying comprises amplification of at least a portion of one or more genomic regions of the soybean genome selected from the group consisting of SEQ ID NOs: 41, 43, 45, 47, 49, 51, 53, and 55.

7. The method of claim 6, wherein the amplification comprises providing one or more nucleic acid primers, wherein the nucleic acid primers comprise the nucleic acid sequence selected from the group consisting of SEQ ID NOs: 1, 2, 5, 6, 9, 10, 13, 14, 17, 18, 21, 22, 25, 26, 29, and 30.

8. The method of claim 7, wherein the detecting further comprises hybridization with one or more nucleic acid probes, wherein the nucleic acid probes comprise the nucleic acid sequence selected from the group consisting of SEQ ID NOs: 3, 4, 7, 8, 11, 12, 15, 16, 19, 20, 23, 24, 27, 28, 31, and 32.

9. The method of any of claims 1, 2 and 3, further comprising:
   before, simultaneous with or after step (b) and before step (c), the further step of detecting in the soybean plant or soybean germplasm at least one allele of one or more marker locus within or linked to a QTL associated with days to maturity, wherein the allele is favorable for a second reproductive growth phenotype selected from the group consisting of early maturity, mid maturity and late maturity; and
   after step (b) and before, simultaneous with or after step (c), the further step of selecting the soybean plant or soybean germplasm comprising the allele of one or more marker locus within or linked to the QTL associated with days to maturity, thereby selecting a soybean plant with a second reproductive growth phenotype selected from the group consisting of early maturity, mid maturity and late maturity.

10. The method of claim 9, wherein the one or more marker locus within or linked to the QTL associated with days to maturity is selected from the group consisting of marker locus M1 and marker locus M2.

11. The method of claim 10, wherein the soybean plant or soybean germplasm comprises: (i) allele T of marker locus M1; (ii) allele T of marker locus M2; (iii) allele T of marker locus M1 and allele T of marker locus M2; or (iv) allele T of marker locus M1 and allele C of marker locus M2.

12. The method of claim 10, wherein the soybean plant or soybean germplasm comprises: (i) allele C of marker locus M1; (ii) allele C of marker locus M2; or (iii) allele C of marker locus M1 and allele C of marker locus M2.

13. The method of claim 9, wherein detecting each allele comprises amplifying a nucleic acid sequence comprising the marker locus of each said allele and detecting the resulting amplified nucleic acid comprising each marker locus.

14. The method of claim 13, wherein the amplifying comprises amplification of at least a portion of one or more genomic regions of the soybean genome selected from the group consisting of SEQ ID NOs: 57 and 59.

15. The method of claim 14, wherein the amplification comprises providing one or more nucleic acid primers, wherein the nucleic acid primers comprise the nucleic acid sequence selected from the group consisting of SEQ ID NOs: 33, 34, 37, and 38.

16. The method of claim 15, wherein the detecting further comprises hybridization with one or more nucleic acid probes, wherein the nucleic acid probes comprise the nucleic acid sequence selected from the group consisting of SEQ ID NOs: 35, 36, 39, and 40.

17. The method of any one of claims 1, 2, 3 and 9, further comprising crossing the selected soybean plant or soybean germplasm with a recurrent soybean parent to produce a population of progeny soybean germplasm, whereby the QTL associated with days to initiation of flowering, the QTL associated with days to maturity, or both, is introgressed into a subpopulation of the progeny soybean germplasm.

18. The method of claim 17, further comprising genotyping the population of progeny soybean germplasm, detecting in a subpopulation of progeny soybean germplasm:
   (i) an allele of at least one marker locus linked to the QTL associated with days to initiation of flowering;
   (ii) an allele of at least one marker locus linked to the QTL associated with days to maturity;
   (iii) or both; and
selecting the subpopulation of progeny soybean germplasm comprising (i), (ii), or (iii).

19. The method of claim 18, wherein a progeny soybean plant grown from the subpopulation of progeny soybean germplasm displays an altered reproductive growth phenotype as compared to the recurrent soybean parent, and wherein the altered reproductive growth phenotype comprises:

(i) increased number of days from planting to initiation of flowering as compared to the recurrent soybean parent;
(ii) decreased number of days from planting to initiation of flowering as compared to the recurrent soybean parent;
(iii) decreased number of days from planting to maturity as compared to the recurrent soybean parent;
(iv) increased number of days from planting to maturity as compared to the recurrent soybean parent;
(v) decreased number of days from planting to initiation of flowering as compared to the recurrent soybean parent and decreased number of days from planting to maturity as compared to the recurrent soybean parent;
(vi) decreased number of days from planting to initiation of flowering as compared to the recurrent soybean parent and increased number of days from planting to maturity as compared to the recurrent soybean parent;
(vii) increased number of days from planting to initiation of flowering as compared to the recurrent soybean parent and the same average number of days from planting to maturity as compared to the recurrent soybean parent; or
(vii) decreased number of days from planting to initiation of flowering as compared to the recurrent soybean parent and the same average number of days from planting to maturity as compared to the recurrent soybean parent.

20. The method of claim 18, wherein a progeny soybean plant grown from the subpopulation of progeny soybean germplasm displays:
(i) increased number of days from planting to initiation of flowering as compared to a soybean plant not comprising the allele of at least one marker locus linked to the QTL associated with days to initiation of flowering;
(ii) decreased number of days from planting to initiation of flowering as compared to a soybean plant not comprising the allele of at least one marker locus linked to the QTL associated with days to initiation of flowering;
(iii) decreased number of days from planting to maturity as compared to a soybean plant not comprising the allele of at least one marker locus linked to the QTL associated with days to maturity;
(iv) increased number of days from planting to maturity as compared to a soybean plant not comprising the allele of at least one marker locus linked to the QTL associated with days to maturity;
(v) decreased number of days from planting to initiation of flowering and decreased number of days from planting to maturity as compared to a soybean plant not comprising the allele of at least one marker locus linked to the QTL associated with days to initiation of flowering or the allele of at least one marker locus linked to the QTL associated with days to maturity; or
(vi) decreased number of days from planting to initiation of flowering and increased number of days from planting to maturity as compared to a soybean plant not comprising the allele of at least one marker locus linked to the QTL associated with days to initiation of flowering or the allele of at least one marker locus linked to the QTL associated with days to maturity; and
wherein the soybean plant of (i)-(vi) is grown in the same field as the progeny soybean plant.

21. A method of selecting a soybean plant or soybean germplasm with an extended reproductive growth stage, the method comprising:
(a) isolating a first polynucleotide from the soybean plant or soybean germplasm, wherein the first polynucleotide comprises allele A at marker locus F5 on chromosome 18;
(b) selecting the soybean plant or soybean germplasm comprising the at least one allele from step (a), thereby selecting a soybean plant with early flowering; and
(c) crossing the selected soybean plant or soybean germplasm with a recurrent soybean parent to produce a population of progeny soybean germplasm, whereby the QTL associated with days to initiation of flowering is introgressed into a subpopulation of the progeny soybean germplasm.

22. The method of claim 21, further comprising:
before, simultaneous with or after step (a) and before step (b), the further step of isolating a second polynucleotide from the soybean plant or soybean germplasm, wherein the second polynucleotide comprises at least one allele of one or more marker locus within or linked to a QTL associated with days to maturity, wherein the allele is favorable for a reproductive growth phenotype selected from the group consisting of early maturity, mid maturity and late maturity, and wherein the one or more marker locus within or linked to the QTL associated with days to maturity phenotype is selected from the group consisting of marker locus M1 and marker locus M2; and
after step (a) and before, simultaneous with or after step (b), the further step of selecting the soybean plant or soybean germplasm comprising the allele of one or more marker locus within or linked to the QTL associated with days to maturity, thereby selecting a soybean plant with a reproductive growth phenotype selected from the group consisting of early maturity, mid maturity and late maturity.

23. A method of selecting a soybean plant or soybean germplasm with an extended reproductive growth stage, the method comprising:
(a) isolating nucleic acids from a genome of a first soybean plant or soybean germplasm;
(b) detecting in the first soybean plant or first soybean germplasm at least one allele of marker locus F5 on chromosome 18 favorable for a first reproductive growth phenotype selected from the group consisting of early flowering and late flowering, wherein the at least one allele favorable for early flowering is allele A at marker locus F5 on chromosome 18 and the at least one favorable allele for late flowering is allele C at marker locus F5 on chromosome 18;
(c) detecting in the soybean plant or soybean germplasm at least one favorable allele of one or more marker locus within or linked to a QTL associated with days to maturity, wherein the allele is favorable for a reproductive growth phenotype selected from the group consisting of mid maturity and late maturity, and wherein the one or more marker locus is selected from the group consisting of marker locus M1 and marker locus M2
(d) selecting the soybean plant or soybean germplasm comprising the at least one allele from step (b) and the at least one allele from step (c), thereby selecting a soybean plant with early flowering and mid or late maturity; and
(e) crossing the selected soybean plant or soybean germplasm with a recurrent soybean parent to produce a population of progeny soybean germplasm, whereby the QTL associated with days to initiation of flowering, and the QTL associated with days to maturity is introgressed into a subpopulation of the progeny soybean germplasm.

24. The method of claim 23, wherein the soybean plant or soybean germplasm comprises two or more of allele T of marker locus F2, allele A of marker locus F5, allele A of marker locus F6, allele G of marker locus F7, or allele G of marker locus F8, and wherein a haplotype defined by the alleles confers early flowering to the soybean plant or soybean germplasm.

25. The method of claim 24, wherein the soybean plant or soybean germplasm comprises: (i) allele T of marker locus M1; (ii) allele T of marker locus M2;
  (iii) allele T of marker locus M1 and allele T of marker locus M2; or (iv) allele T of marker locus M1 and allele C of marker locus M2, and wherein a haplotype defined by the alleles confers mid or late maturity to the soybean plant or soybean germplasm.

26. The method of claim 24 or 25, wherein the soybean plant or soybean germplasm displays increased yield.

* * * * *

SEQUENCE LISTING

```
<160> NUMBER OF SEQ ID NOS: 60

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide Primer/probe

<400> SEQUENCE: 1
ttgtctgtgc tccttagaca tca                                             23

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide Primer/probe

<400> SEQUENCE: 2
ttgagctatt ggtgttttgc tc                                              22
```

<210> SEQ ID NO 3
<211> LENGTH: 14
<212> TYPE: DNA
<213> ORGANISM: Artificial Sequence
<220> FEATURE:
<223> OTHER INFORMATION: Oligonucleotide Primer/probe

<400> SEQUENCE: 3
caactgcacc aagg                                                    14

<210> SEQ ID NO 4
<211> LENGTH: 15
<212> TYPE: DNA
<213> ORGANISM: Artificial Sequence
<220> FEATURE:
<223> OTHER INFORMATION: Oligonucleotide Primer/probe

<400> SEQUENCE: 4
caactgcacc acgga                                                   15

<210> SEQ ID NO 5
<211> LENGTH: 23
<212> TYPE: DNA
<213> ORGANISM: Artificial Sequence
<220> FEATURE:
<223> OTHER INFORMATION: Oligonucleotide Primer/probe

<400> SEQUENCE: 5
cgtttcgttt taccactctt tca                                          23

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide Primer/probe

<400> SEQUENCE: 6
acccttcaat tgcagaaagc                                              20

<210> SEQ ID NO 7
<211> LENGTH: 14
<212> TYPE: DNA
<213> ORGANISM: Artificial Sequence
<220> FEATURE:
<223> OTHER INFORMATION: Oligonucleotide Primer/probe

<400> SEQUENCE: 7
cttgccctca atct                                                    14

<210> SEQ ID NO 8
<211> LENGTH: 16
<212> TYPE: DNA
<213> ORGANISM: Artificial Sequence
<220> FEATURE:
<223> OTHER INFORMATION: Oligonucleotide Primer/probe

<400> SEQUENCE: 8
ccctcattct gtttgt                                                  16

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide Primer/probe

```
<400> SEQUENCE: 9
caacacacac ggaaaattgg                                                 20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide Primer/probe

<400> SEQUENCE: 10
ggttccaaat tcacctttcg                                                 20

<210> SEQ ID NO 11
<211> LENGTH: 14
<212> TYPE: DNA
<213> ORGANISM: Artificial Sequence
<220> FEATURE:
<223> OTHER INFORMATION: Oligonucleotide Primer/probe

<400> SEQUENCE: 11
aggacccttt tgca                                                       14

<210> SEQ ID NO 12
<211> LENGTH: 16
<212> TYPE: DNA
<213> ORGANISM: Artificial Sequence
<220> FEATURE:
<223> OTHER INFORMATION: Oligonucleotide Primer/probe

<400> SEQUENCE: 12 aaggacccttt tggcaa                                                    16

<210> SEQ ID NO 13
<211> LENGTH: 23
<212> TYPE: DNA
<213> ORGANISM: Artificial Sequence
<220> FEATURE:
<223> OTHER INFORMATION: Oligonucleotide Primer/probe

<400> SEQUENCE: 13
cacattatag gggccttttg tta                                             23

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide Primer/probe

<400> SEQUENCE: 14
ttgcatattt tctcccacct g                                               21

<210> SEQ ID NO 15
<211> LENGTH: 18
<212> TYPE: DNA
<213> ORGANISM: Artificial Sequence
<220> FEATURE:
<223> OTHER INFORMATION: Oligonucleotide Primer/probe

<400> SEQUENCE: 15
caaattaaca catcaaca                                                   18
```

```
<210> SEQ ID NO 16
<211> LENGTH: 18
<212> TYPE: DNA
<213> ORGANISM: Artificial Sequence
<220> FEATURE:
<223> OTHER INFORMATION: Oligonucleotide Primer/probe

<400> SEQUENCE: 16
caaattaaca cgtcaaca                                                   18

<210> SEQ ID NO 17
<211> LENGTH: 26
<212> TYPE: DNA
<213> ORGANISM: Artificial Sequence
<220> FEATURE:
<223> OTHER INFORMATION: Oligonucleotide Primer/probe

<400> SEQUENCE: 17
tgtattatta tcaaaatgag gggttg                                          26

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide Primer/probe

<400> SEQUENCE: 18
caacctactt caactgtaaa cgtca                                           25

<210> SEQ ID NO 19
<211> LENGTH: 14
<212> TYPE: DNA
<213> ORGANISM: Artificial Sequence
<220> FEATURE:
<223> OTHER INFORMATION: Oligonucleotide Primer/probe

<400> SEQUENCE: 19
cttccagctc ttgc                                                       14

<210> SEQ ID NO 20
<211> LENGTH: 15
<212> TYPE: DNA
<213> ORGANISM: Artificial Sequence
<220> FEATURE:
<223> OTHER INFORMATION: Oligonucleotide Primer/probe

<400> SEQUENCE: 20
cttccatctc ttgcg                                                      15

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide Primer/probe

<400> SEQUENCE: 21
ttgaggtatc ttttatcttc aggaaag                                         27

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide Primer/probe
```

<400> SEQUENCE: 22
gcattgccat gagaatgtaa ct                                              22

<210> SEQ ID NO 23
<211> LENGTH: 17
<212> TYPE: DNA
<213> ORGANISM: Artificial Sequence
<220> FEATURE:
<223> OTHER INFORMATION: Oligonucleotide Primer/probe

<400> SEQUENCE: 23
ctccaacttt tattctc                                                    17

<210> SEQ ID NO 24
<211> LENGTH: 17
<212> TYPE: DNA
<213> ORGANISM: Artificial Sequence
<220> FEATURE:
<223> OTHER INFORMATION: Oligonucleotide Primer/probe

<400> SEQUENCE: 24
ctccaacttt tgttctc                                                    17

<210> SEQ ID NO 25
<211> LENGTH: 21
<212> TYPE: DNA
<213> ORGANISM: Artificial Sequence
<220> FEATURE:
<223> OTHER INFORMATION: Oligonucleotide Primer/probe

<400> SEQUENCE: 25
cctatgaaag tccacgtcca a                                               21

<210> SEQ ID NO 26
<211> LENGTH: 28
<212> TYPE: DNA
<213> ORGANISM: Artificial Sequence
<220> FEATURE:
<223> OTHER INFORMATION: Oligonucleotide Primer/probe

<400> SEQUENCE: 26
caagattata aatctcagca aagtctct                                        28

<210> SEQ ID NO 27
<211> LENGTH: 14
<212> TYPE: DNA
<213> ORGANISM: Artificial Sequence
<220> FEATURE:
<223> OTHER INFORMATION: Oligonucleotide Primer/probe

<400> SEQUENCE: 27
ctgcctagac taac                                                       14

<210> SEQ ID NO 28
<211> LENGTH: 14
<212> TYPE: DNA
<213> ORGANISM: Artificial Sequence
<220> FEATURE:
<223> OTHER INFORMATION: Oligonucleotide Primer/probe

<400> SEQUENCE: 28
ctgcgtagac taac                                                       14

```
<210> SEQ ID NO 29
<211> LENGTH: 22
<212> TYPE: DNA
<213> ORGANISM: Artificial Sequence
<220> FEATURE:
<223> OTHER INFORMATION: Oligonucleotide Primer/probe

<400> SEQUENCE: 29
cactgctttg atcattttct cg                                              22

<210> SEQ ID NO 30
<211> LENGTH: 19
<212> TYPE: DNA
<213> ORGANISM: Artificial Sequence
<220> FEATURE:
<223> OTHER INFORMATION: Oligonucleotide Primer/probe

<400> SEQUENCE: 30
ggcgccagaa tttcaacac                                                  19

<210> SEQ ID NO 31
<211> LENGTH: 18
<212> TYPE: DNA
<213> ORGANISM: Artificial Sequence
<220> FEATURE:
<223> OTHER INFORMATION: Oligonucleotide Primer/probe

<400> SEQUENCE: 31
ctggtaattc aagattat                                                   18

<210> SEQ ID NO 32
<211> LENGTH: 16
<212> TYPE: DNA
<213> ORGANISM: Artificial Sequence
<220> FEATURE:
<223> OTHER INFORMATION: Oligonucleotide Primer/probe

<400> SEQUENCE: 32
ctggtaatcc aagatt                                                     16

<210> SEQ ID NO 33
<211> LENGTH: 23
<212> TYPE: DNA
<213> ORGANISM: Artificial Sequence
<220> FEATURE:
<223> OTHER INFORMATION: Oligonucleotide Primer/probe

<400> SEQUENCE: 33
ccttaatttg gaatcctatg ctg                                             23

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide Primer/probe

<400> SEQUENCE: 34
aagtggcttt tggtccaatg                                                 20

<210> SEQ ID NO 35
<211> LENGTH: 17
<212> TYPE: DNA
<213> ORGANISM: Artificial Sequence
<220> FEATURE:
<223> OTHER INFORMATION: Oligonucleotide Primer/probe
```

```
<400> SEQUENCE: 35
aaccttcgtt gtgtgct                                                        17

<210> SEQ ID NO 36
<211> LENGTH: 18
<212> TYPE: DNA
<213> ORGANISM: Artificial Sequence
<220> FEATURE:
<223> OTHER INFORMATION: Oligonucleotide Primer/probe

<400> SEQUENCE: 36
aaccttcgtt atgtgctt                                                       18

<210> SEQ ID NO 37
<211> LENGTH: 25
<212> TYPE: DNA
<213> ORGANISM: Artificial Sequence
<220> FEATURE:
<223> OTHER INFORMATION: Oligonucleotide Primer/probe

<400> SEQUENCE: 37
actacactaa atctccccag tacga                                               25

<210> SEQ ID NO 38
<211> LENGTH: 27
<212> TYPE: DNA
<213> ORGANISM: Artificial Sequence
<220> FEATURE:
<223> OTHER INFORMATION: Oligonucleotide Primer/probe

<400> SEQUENCE: 38
gcctacttat gtctttatca cttcaca                                             27

<210> SEQ ID NO 39
<211> LENGTH: 16
<212> TYPE: DNA
<213> ORGANISM: Artificial Sequence
<220> FEATURE:
<223> OTHER INFORMATION: Oligonucleotide Primer/probe

<400> SEQUENCE: 39
aagcattgag tcctac                                                         16

<210> SEQ ID NO 40
<211> LENGTH: 16
<212> TYPE: DNA
<213> ORGANISM: Artificial Sequence
<220> FEATURE:
<223> OTHER INFORMATION: Oligonucleotide Primer/probe

<400> SEQUENCE: 40
aagcattgaa tcctac                                                         16

<210> SEQ ID NO 41
<211> LENGTH: 488
<212> TYPE: DNA
<213> ORGANISM: Glycine max
<220> FEATURE:
<221> NAME/KEY: variation
<222> LOCATION: (155)..(155)
<223> OTHER INFORMATION: SNP F1

<400> SEQUENCE: 41
taaagctaat tactttattt actaagaaac aatgataatt tcacattaga ttggagtcac         60
tccatttata ttgcacagtw tgcaaamttt gaattgtctg tgctccttag acatcaccaa        120
```

```
ttagtactct acttctgtta tagcaactgc accamggaac asddtcctat atcaataagg      180
ataggtttgg gagcaaaaca ccaatagctc aaagtaacat cttttttttct tatttaaatt    240 catcttttgc tcctgctttt tctacataaa caaatgttca tgatccctttt tatgcaatag   300 tgaataaaag atgcgttttg tawcaaccgg aaacataaaa tgctcatttc ttckataatt    360
aaaaaaagta ggcagygaga agtaaaaata tatactagca tattacccct tggattgaca   420
aaggggagaa acaaaatttt accacatgta agcaagcaca caaactctaa acacaacatg   480
gtcatagc                                                              488

<210> SEQ ID NO 42
<211> LENGTH: 119
<212> TYPE: DNA
<213> ORGANISM: Glycine max
<220> FEATURE:
<221> NAME/KEY: variation
<222> LOCATION: (62)..(62)
<223> OTHER INFORMATION: SNP F1

<400> SEQUENCE: 42
ttgtctgtgc tccttagaca tcaccaatta gtactctact tctgttatag caactgcacc     60
amggaacasd dtcctatatc aataaggata ggtttgggag caaaacacca atagctcaa    119

<210> SEQ ID NO 43
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP F2

<400> SEQUENCE: 43
cagcaactac cagattcttt gccttaggtg gaaggctcct atatcctaaa agtccagcca     60
tcttgatcaa tgggggaaaa aagggttagc acaatttcac acaattacaa ttacccttca   120
attgcagaaa gcacaaaaga tcacaaaaca aataattcaa atctgtaaga aaataatgag   180
tagacatttc cacaaacaga wtgagggcaa ggcaatccta acacaacaca attgaaagag   240
tggtaaaacg aaacgtattg agaggtgatt aaattgtttc atcaaacaga aacagttttg   300
atgggtacta ctaatattgc tacaaagaaa acctttcaat taagtttcta tgatatgaag   360
cagacagcat tagcaccatc aaaatttcag aaatgatgac a                       401

<210> SEQ ID NO 44
<211> LENGTH: 143
<212> TYPE: DNA
<213> ORGANISM: Glycine max
<220> FEATURE:
<221> NAME/KEY: variation
<222> LOCATION: (89)..(89)
<223> OTHER INFORMATION: SNP F2

<400> SEQUENCE: 44
acccttcaat tgcagaaagc acaaagatc acaaaacaaa taattcaaat ctgtaagaaa      60
ataatgagta gacatttcca caaacagawt gagggcaagg caatcctaac acaacacaat   120
tgaaagagtg gtaaaacgaa acg                                            143

<210> SEQ ID NO 45
<211> LENGTH: 121
<212> TYPE: DNA
<213> ORGANISM: Glycine max
```

```
<220> FEATURE:
<221> NAME/KEY: variation
<222> LOCATION: (61)..(61)
<223> OTHER INFORMATION: SNP F3

<400> SEQUENCE: 45
ctatcmacct gcaacaacac acacggaaaa ttggtcacac aaagagaaaa aggaccctttt    60 kgcaatgcag aaaagacaaa gccaacgaaa ggtgaatttg gaacctttat gacagtgtct   120
g                                                                   121

<210> SEQ ID NO 46
<211> LENGTH: 91
<212> TYPE: DNA
<213> ORGANISM: Glycine max
<220> FEATURE:
<221> NAME/KEY: variation
<222> LOCATION: (47)..(47)
<223> OTHER INFORMATION: SNP F3

<400> SEQUENCE: 46
caacacacac ggaaaattgg tcacacaaag agaaaaagga ccctttkgca atgcagaaaa    60
gacaaagcca acgaaaggtg aatttggaac c                                   91

<210> SEQ ID NO 47
<211> LENGTH: 595
<212> TYPE: DNA
<213> ORGANISM: Glycine max
<220> FEATURE:
<221> NAME/KEY: variation
<222> LOCATION: (248)..(248)
<223> OTHER INFORMATION: SNP F4

<400> SEQUENCE: 47
gttgattggc tactaaaaca aatgctatat ttgtaaatat ataccaatat agcaatacag    60
gggtaattga aaattctgat taactgttaa tctacaggtt aacagtcttc ggcaggaact   120
acaacttctt gctagagata gatcaatcac tattgtaaat gcaagtggaa caggtactgg   180
ttagctactt tcttatacac attatagggg cctttttgtta tttcttcagc aatttaataa   240
atgttgaygt gttaatttgc aaacccatga taactggttt taattgtggg ctgtctccat   300
actctacaca agctaaacaa tgtttcctta ttatttttta ctcctgtttt attttctgac   360
ttgtttggga aatgcacagg tgggagaaaa tatgcaacag tgattgttat tgttgtggta   420
ggatatggat acgtttggtg gaaggtaatg tcttttctct ctcaattgtt gatttaagta   480
acaggatgct gtagtgatac attcttgttg gaagctttat ggctaatttg aatttaaata   540
ttggtgctta taacgagtgc catctgctct ttgcacatgg atactctcca cttaa         595

<210> SEQ ID NO 48
<211> LENGTH: 200
<212> TYPE: DNA
<213> ORGANISM: Glycine max
<220> FEATURE:
<221> NAME/KEY: variation
<222> LOCATION: (51)..(51)
<223> OTHER INFORMATION: SNP F4

<400> SEQUENCE: 48
cacattatag gggccttttg ttatttcttc agcaatttaa taaatgttga ygtgttaatt    60
tgcaaaccca tgataactgg ttttaattgt gggctgtctc catactctac acaagctaaa   120
```
caatgtttcc ttattatttt ttactcctgt tttattttct gacttgtttg ggaaatgcac    180
aggtgggaga aaatatgcaa    200

<210> SEQ ID NO 49
<211> LENGTH: 401
<212> TYPE: DNA
<213> ORGANISM: Glycine max
<220> FEATURE:
<221> NAME/KEY: other
<222> LOCATION: (4)..(4)
<223> OTHER INFORMATION: N = a, c, t or g
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: other
<222> LOCATION: (10)..(10)
<223> OTHER INFORMATION: N = a, c, t or g
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: other
<222> LOCATION: (58)..(58)
<223> OTHER INFORMATION: N = a, c, t or g
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: other
<222> LOCATION: (137)..(137)
<223> OTHER INFORMATION: N = a, c, t or g
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: variation
<222> LOCATION: (201)..(201)
<223> OTHER INFORMATION: SNP F5
<220> FEATURE:
<221> NAME/KEY: other
<222> LOCATION: (277)..(277)
<223> OTHER INFORMATION: N = a, c, t or g
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: other
<222> LOCATION: (401)..(401)
<223> OTHER INFORMATION: N = a, c, t or g
<220> FEATURE:
<221> NAME/KEY: misc_feature
<222> LOCATION: (401)..(401)
<223> OTHER INFORMATION: n is a, c, g, or t

<400> SEQUENCE: 49
gagntatgan agtccacgac cgatgatggg aattcatcgt attattttca tattattncg    60
tcagtcaggt agacaaacta tatatgctcc aggatggcgt caaaatttca acacgagaga    120
tttcagcgag gtttatnatc ttggattacc agtggcagca acctacttca actgtaaacg    180
tcaaaataat tccgcaagag mtggaagaag gacatgatta ataattaatt caaataatag    240
tcaacccctc attttgataa taatacatta ttgtagntac gtagtaatat atacattact    300
cgggagctag acactcaaat tgttgggttt actttaatag tgattttata caatattcat    360
ttaactgctt tgttattttt tatttctagt tttatcccct n    401

```
<210> SEQ ID NO 50
<211> LENGTH: 109
<212> TYPE: DNA
<213> ORGANISM: Glycine max
<220> FEATURE:
<221> NAME/KEY: variation
<222> LOCATION: (43)..(43)
<223> OTHER INFORMATION: SNP F5

<400> SEQUENCE: 50
caacctactt caactgtaaa cgtcaaaata attccgcaag agmtggaaga aggacatgat    60
taataattaa ttcaaataat agtcaacccc tcattttgat aataataca              109

<210> SEQ ID NO 51
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP F6

<400> SEQUENCE: 51
cctagagtgt cgcactccaa gccaaaatat aaactaagtt ctttgatact atctccgatt    60 cttttatat aggtaggaat atgaaatttt ttatataaag gtaggaatgt ttgttctcat   120
atttgttagg aatttatttg aagatatttt gaggtatctt ttatcttcag gaaagttgta   180
ttttcatgtc tccaactttt rttctcatgt taatggggtg tcaaagttac attctcatgg   240
caatgcaagt aattattttt taaatccatt ataactttta tttttcatat attgttttaa   300
aactttaaaa aacatttcta ggaatgttaa aaggtaacca aaagaacaat tacaatctgt   360
ctctctagga acaagttgat ttttgaaaat gatcaatttt c                       401

<210> SEQ ID NO 52
<211> LENGTH: 98
<212> TYPE: DNA
<213> ORGANISM: Glycine max
<220> FEATURE:
<221> NAME/KEY: variation
<222> LOCATION: (53)..(53)
<223> OTHER INFORMATION: SNP F6

<400> SEQUENCE: 52
ttgaggtatc ttttatcttc aggaaagttg tattttcatg tctccaactt ttrttctcat    60
gttaatgggg tgtcaaagtt acattctcat ggcaatgc                            98

<210> SEQ ID NO 53
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP F7

<400> SEQUENCE: 53
agaaatagta aatattttga ttaagctata aaatttgtgt catgctgtaa tagactgtct    60
ttgaactgtt atcaatatat gtggatttat ttattacttc aataaagggt aatttacagg   120
agaagagatk gtctcctatg aaagtccacg tccaatagta gggattcatc gaatagtttt   180
tgtgttattt cgtcagctgc stagactaac tctgcaacct ccaggstggc gccagaattt   240
caacacyaga gactttgctg agatttataa tcttgratta ccagtmgcgg ccatgtactt   300
```
caactgtaaa cgagaaaatg atcaaagcag tggaagaaga agataataga aagaaaacta        360
ttattaatat atatyccgag tttttatcag ctcaacatga a                            401

<210> SEQ ID NO 54
<211> LENGTH: 141
<212> TYPE: DNA
<213> ORGANISM: Glycine max
<220> FEATURE:
<221> NAME/KEY: variation
<222> LOCATION: (67)..(67)
<223> OTHER INFORMATION: SNP F7

<400> SEQUENCE: 54
cctatgaaag tccacgtcca atagtaggga ttcatcgaat agttttgtg ttatttcgtc         60 agctgcstag actaactctg caacctccag gstggcgcca gaatttcaac acyagagact        120
ttgctgagat ttataatctt g                                                  141

<210> SEQ ID NO 55
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP F8

<400> SEQUENCE: 55
tatatgtgga tttatttatt acttcaataa agggtaattt acaggagaag agatkgtctc        60
ctatgaaagt ccacgtccaa tagtagggat tcatcgaata gttttgtgt tatttcgtca         120 gctgcstaga ctaactctgc aacctccagg stggcgccag aatttcaaca cyagagactt       180
tgctgagatt tataatcttg rattaccagt mgcggccatg tacttcaact gtaaacgaga       240
aaatgatcaa agcagtggaa gaagaagata atagaaagaa aactattatt aatatataty      300
ccgagttttt atcagctcaa catgaaataa taaataactt cttttatat ttaagtattt        360 attaaatata aatatatatt ataaaaaaa atcaacacga a                             401

<210> SEQ ID NO 56
<211> LENGTH: 105
<212> TYPE: DNA
<213> ORGANISM: Glycine max
<220> FEATURE:
<221> NAME/KEY: variation
<222> LOCATION: (49)..(49)
<223> OTHER INFORMATION: SNP F8

<400> SEQUENCE: 56
ggcgccagaa tttcaacacy agagactttg ctgagattta atcttgra ttaccagtmg          60 cggccatgta cttcaactgt aaacgagaaa atgatcaaag cagtg                        105

<210> SEQ ID NO 57
<211> LENGTH: 400
<212> TYPE: DNA
<213> ORGANISM: Glycine max
<220> FEATURE:
<221> NAME/KEY: variation
<222> LOCATION: (201)..(201)
<223> OTHER INFORMATION: SNP M1

<400> SEQUENCE: 57
ctatttrcgg gcaaaactcc tttcattatc atatgaatta agcaattaaa ttgcaccaaa        60
tatgctacca attacagtag gaaggccacg tgttggctaa gcgactcacc tttcacatag       120

```
tcatgttccc ccattatacc ttaatttgga atcctatgct gaaaattatg gtcagtttca      180
ttgaacaatt ttaaagcaca yaacgaaggt tggtaaaaaa acaaaatata ccattctttt      240
caaatgtatt ctaataataa tcaatctaca tgcatgtaat ctaaatccrg aattaaggat      300
ttataattaa tcatacagct gttggactag cattggacca aaagccactt tcaagggaac      360
aacaaagcac tcctgtttat tttattttat ttwttttgtct                          400

<210> SEQ ID NO 58
<211> LENGTH: 212
<212> TYPE: DNA
<213> ORGANISM: Glycine max
<220> FEATURE:
<221> NAME/KEY: variation
<222> LOCATION: (63)..(63)
<223> OTHER INFORMATION: SNP M1

<400> SEQUENCE: 58
ccttaatttg gaatcctatg ctgaaaatta tggtcagttt cattgaacaa ttttaaagca       60
cayaacgaag gttggtaaaa aacaaaata taccattctt ttcaaatgta ttctaataat      120
aatcaatcta catgcatgta atctaaatcc rgaattaagg atttataatt aatcatacag      180
ctgttggact agcattggac caaaagccac tt                                   212

<210> SEQ ID NO 59
<211> LENGTH: 401
<212> TYPE: DNA
<213> ORGANISM: Glycine max
<220> FEATURE:
<221> NAME/KEY: variation
<222> LOCATION: (201)..(201)
<223> OTHER INFORMATION: SNP M2

<400> SEQUENCE: 59
atgytttctt tctaattaat tatgggwacw yaaaaaatta tggatrcata tagatttttc       60
tttataagct tatactacac taaatctccc cagtacgatr gaaattatac gatatacgat      120
atattattaa agaaaagat gatatcattt ataataaaaa aatgtccaac ttacgmaata       180
aggaagtaaa ttgagtagga ytcaatgctt tactaaatmc tcccagacaa tgctttaata      240
aaaaaattgt cactttccaa ttgtgaagtg ataaagacat aagtaggctt aatgtttctc      300
tttagaatct catcccaaac aaattgacaa ttaacttcaa tatattttga tacactttg      360 aaaactaagt atttgtattg tgggatgtta cttkgttatc g                         401

<210> SEQ ID NO 60
<211> LENGTH: 215
<212> TYPE: DNA
<213> ORGANISM: Glycine max
<220> FEATURE:
<221> NAME/KEY: variation
<222> LOCATION: (128)..(128)
<223> OTHER INFORMATION: SNP M2

<400> SEQUENCE: 60
actacactaa atctccccag tacgatrgaa attatacgat atacgatata ttattaaaag       60
aaaagatgat atcatttata ataaaaaaat gtccaactta cgmaataagg aagtaaattg      120
agtaggaytc aatgctttac taaatmctcc cagacaatgc tttaataaaa aaattgtcac      180
tttccaattg tgaagtgata agacataag taggc                                 215
```